United States Patent
Murakoshi et al.

(10) Patent No.: US 10,243,318 B2
(45) Date of Patent: Mar. 26, 2019

(54) LASER DEVICE AND PHOTOACOUSTIC MEASUREMENT DEVICE COMPRISING THE SAME

(71) Applicant: FUJIFILM Corporation, Tokyo (JP)

(72) Inventors: Dai Murakoshi, Ashigarakami-gun (JP); Kaku Irisawa, Ashigarakami-gun (JP); Takuji Tada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 277 days.

(21) Appl. No.: 15/275,697

(22) Filed: Sep. 26, 2016

(65) Prior Publication Data

US 2017/0012403 A1    Jan. 12, 2017

Related U.S. Application Data

(63) Continuation of application No. PCT/JP2015/053270, filed on Feb. 5, 2015.

(30) Foreign Application Priority Data

Mar. 27, 2014    (JP) .................................. 2014-065958

(51) Int. Cl.
| | |
|---|---|
| *H01S 3/127* | (2006.01) |
| *H01S 3/092* | (2006.01) |
| *A61B 5/00* | (2006.01) |
| *H01S 3/082* | (2006.01) |

(Continued)

(52) U.S. Cl.
CPC ............ *H01S 3/127* (2013.01); *A61B 5/0095* (2013.01); *H01S 3/082* (2013.01); *H01S 3/0809* (2013.01);

(Continued)

(58) Field of Classification Search
CPC ........ H01S 3/127; H01S 3/0809; H01S 3/082; H01S 3/092; H01S 3/1633; H01S 3/106; A61B 5/0095
See application file for complete search history.

(56) References Cited

U.S. PATENT DOCUMENTS 6,078,606 A * 6/2000 Naiman ................... G03H 1/02
372/108
2005/0004458 A1    1/2005 Kanayama et al.
(Continued)

FOREIGN PATENT DOCUMENTS

| CN | 1983746 A | 6/2007 |
|---|---|---|
| DE | 37 04 338 A1 | 8/1988 |

(Continued)

OTHER PUBLICATIONS

International Search of the Report, issued in PCT/JP2015/053270, dated Apr. 21, 2015.

(Continued)

*Primary Examiner* — Armando Rodriguez
(74) *Attorney, Agent, or Firm* — Birch, Stewart, Kolasch & Birch, LLP

(57) ABSTRACT

In a laser device and a photoacoustic measurement device including the laser device, the intensity of light at each wavelength made independently controllable. The laser device includes a laser medium which has oscillation wavelengths at a first wavelength and a second wavelength with higher light emission efficiency than at the first wavelength, an excitation section, a first resonator, a second resonator, a Q-value change unit, and a control section. The control section oscillates light having the first wavelength through Q switching when a first delay time has elapsed after the excitation of the laser medium has been started in a case where the oscillation wavelength is the first wavelength, and oscillates light having the second wavelength through Q (Continued)

switching when a second delay time has elapsed after the excitation of the laser medium has been started in a case where the oscillation wavelength is the second wavelength.

18 Claims, 11 Drawing Sheets

(51) Int. Cl.
    *H01S 3/08*     (2006.01)
    *H01S 3/16*     (2006.01)
    *H01S 3/106*     (2006.01)

(52) U.S. Cl.
    CPC ............ *H01S 3/092* (2013.01); *H01S 3/1633* (2013.01); *H01S 3/106* (2013.01)

(56) References Cited

U.S. PATENT DOCUMENTS

| | | |
|---|---|---|
| 2010/0049049 A1 | 2/2010 | Asao et al. |
| 2012/0243563 A1 | 9/2012 | Goldberg |
| 2014/0185634 A1 | 7/2014 | Ichihara et al. |
| 2014/0336482 A1 | 11/2014 | Kasamatsu et al. |
| 2015/0005612 A1* | 1/2015 | Suzuki ................ A61B 5/0095 600/407 |

FOREIGN PATENT DOCUMENTS

| | | |
|---|---|---|
| JP | 2005-21380 A | 1/2005 |
| JP | 2005-72131 A | 3/2005 |
| JP | 2005-158790 A | 6/2005 |
| JP | 2010-46215 A | 3/2010 |
| JP | 2013-89680 A | 5/2013 |
| JP | 2013-214703 A | 10/2013 |

OTHER PUBLICATIONS

Written Opinion of the International Searching Authority, issued in PCT/JP2015/053270, dated Apr. 21, 2015.
English Translation of International Preliminary Report on Patentability (including PCT/IB/373 and PC/ISA/237) for PCT/JP2015/053270, dated Sep. 27, 2016.
Chinese Office Action and Search Report for corresponding Chinese Application No. 201580016006.0, dated Jun. 1, 2018, with an English translation of the Office Action.
Extended European Search Report dated Feb. 7, 2017 in corresponding EP Application No. 15768938.1.
European Office Action for corresponding European Application No. 15768938.1, dated Jul. 11, 2018.

* cited by examiner

FIG. 7A  FL TRIGGER 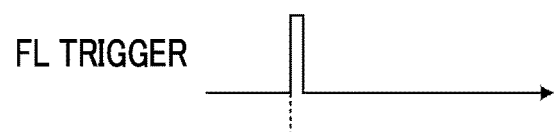
FIG. 7B  FL LIGHT EMISSION 
FIG. 7C  INVERTED DISTRIBUTION STATE DENSITY 
FIG. 7D  Qsw TRIGGER 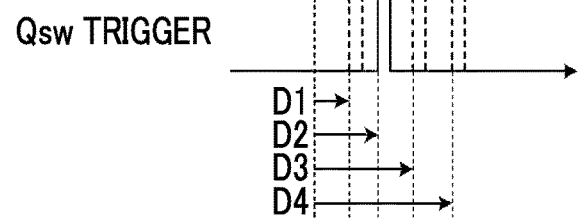
FIG. 7E  LASER LIGHT 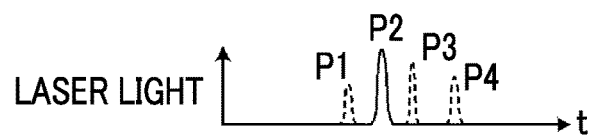

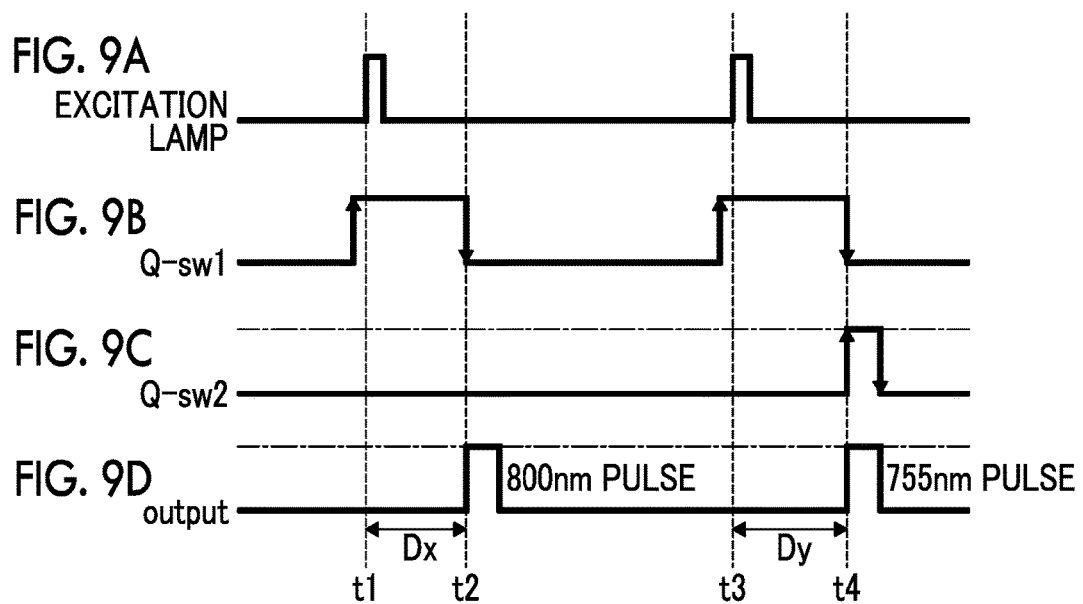

US 10,243,318 B2

LASER DEVICE AND PHOTOACOUSTIC MEASUREMENT DEVICE COMPRISING THE SAME

CROSS-REFERENCE TO RELATED APPLICATIONS

This application is a Continuation of PCT International Application No. PCT/JP2015/053270 filed on Feb. 5, 2015, which claims priority under 35 U.S.C § 119(a) to Japanese Patent Application No. 2014-065958 filed on Mar. 27, 2014. Each of the above application(s) is hereby expressly incorporated by reference, in its entirety, into the present application.

BACKGROUND OF THE INVENTION

1. Field of the Invention

The present invention relates to a laser device, and in particular, to a laser device which is able to emit light having a first wavelength and light having a second wavelength. The present invention also relates to a photoacoustic measurement device comprising the laser device.

2. Description of the Related Art

Hitherto, for example, as shown in JP2005-021380A, a photoacoustic image generation device which images the inside of a living body using a photoacoustic effect is known. In this photoacoustic image generation device, for example, the living body is irradiated with pulse light, such as pulse laser light. Inside the living body irradiated with pulse light, a living body tissue which absorbs energy of pulse light expands in volume due to heat, and an acoustic wave is generated. The acoustic wave is detected by an ultrasound probe or the like, and the inside of the living body can be imaged based on the detected signal (photoacoustic signal). In a photoacoustic image generation method, since an acoustic wave is generated in a specific optical absorber, a specific tissue in the living body, for example, a blood vessel or the like can be imaged.

A large number of living body tissues have an optical absorption characteristic which changes depending on the wavelength of light, and in general, the optical absorption characteristic is peculiar to each tissue. For example, FIG. 14 shows molecular absorption coefficients for each optical wavelength of oxygenated hemoglobin (hemoglobin bonded to oxygen: oxy-Hb) contained in a large amount in a human artery and deoxygenated hemoglobin (hemoglobin not bonded to oxygen: deoxy-Hb) contained in a large amount in a vein. The optical absorption characteristic of the artery corresponds to the optical absorption characteristic of oxygenated hemoglobin, and the optical absorption characteristic of the vein corresponds to the optical absorption characteristic of deoxygenated hemoglobin. A photoacoustic image generation method which irradiates a blood vessel portion with light having two different wavelengths by means of a difference in light absorption depending on wavelength and images the artery and the vein distinctively is known (for example, see JP2010-046215A).

For example, JP2013-089680A and JP2013-214703A describe a variable wavelength laser device which is able to emit light having two wavelengths. The laser device is an alexandrite laser light source which has a flash lamp as an excitation source, and is able to generate laser oscillation at a wavelength of 755 nm and a wavelength of 800 nm.

SUMMARY OF THE INVENTION

In the alexandrite laser light source, light having the wavelength of 755 nm and light having the wavelength of 800 nm are different in light emission efficiency. FIG. 15 is a graph showing the relationship between an oscillation wavelength and light emission efficiency (gain) when alexandrite is used as a laser medium. As will be understood from the graph, for example, light emission efficiency of alexandrite is maximized near the wavelength of 755 nm, and is lowered when the wavelength becomes longer in a wavelength range exceeding the wavelength of 755 nm.

In this way, in a case where a laser medium having two oscillation wavelengths having different light emission efficiencies (for example, a wavelength having low light emission efficiency is referred to as a "first wavelength", and a wavelength having high light emission efficiency is referred to as a "second wavelength") is used, in general, laser light having different intensities is oscillated. For example, if sufficient intensity is desired to be secured for light having the first wavelength, the intensity of light having the second wavelength may exceed a damage threshold of the device. Due to this, it should suffice that, only in a case where the oscillation wavelength is the second wavelength, the excitation energy of the laser medium can be reduced in order to reduce the intensity of light having the second wavelength; however, there is a limit to the reduction of the excitation energy due to the characteristic of the excitation light source or the configuration of the device. The reduction of the excitation energy itself may be undesirable. In addition, as a method of reducing the intensity of light having the second wavelength, for example, a method which makes only light having the second wavelength pass through a dimmer filter is considered. However, in this method, since the dimmer filter or a branch structure of light is required, the number of parts of the device increases, causing an increase in cost.

Accordingly, for example, in this case, there is a demand for a method capable of independently controlling the intensity of light having each wavelength without increasing the number of parts of the device.

The invention has been accomplished in consideration of the above-described demand, and an object of the invention is to provide a laser device which uses a laser medium with two oscillation wavelengths having different light emission efficiencies, having an advantage capable of independently controlling the intensity of light at each wavelength without increasing the number of parts of the device, and a photoacoustic measurement device comprising the laser device.

In order to solve the above-described problem, a laser device of the invention comprises a solid-state laser medium which has oscillation wavelengths at a first wavelength and a second wavelength with higher light emission efficiency than at the first wavelength, an excitation section which excites the laser medium, a first resonator which is a resonator oscillating light having the first wavelength and has the laser medium on an internal optical path, a second resonator which is a resonator oscillating light having the second wavelength and has a common optical path which is an optical path in common for the first resonator including an optical path, on which the laser medium is disposed, a Q-value change unit which includes at least a Q-value change part disposed on the common optical path and oscillates light having the first wavelength or light having the second wavelength through Q switching, and a control section which controls the excitation section and the Q-value change unit. The control section controls the Q-value change unit to oscillate light having the first wavelength through Q switching when a first delay time has elapsed after the excitation of the laser medium has been started in a case where the oscillation wavelength is the first wavelength, and the control section controls the Q-value change unit to oscillate light having the second wavelength through Q switching when a second delay time, at which the intensity of light having the second wavelength is less than possible maximum intensity, has elapsed after the excitation of the laser medium has been started in a case where the oscillation wavelength is the second wavelength.

In the laser device of the invention, it is preferable that the first delay time and the second delay time are set to values such that the intensity of light having the first wavelength and the intensity of light having the second wavelength are equal to each other.

In the laser device of the invention, it is preferable that the first delay time is set to a value such that the intensity of light having the first wavelength becomes the possible maximum intensity.

In the laser device of the invention, it is preferable that the control section changes the set value of the first delay time or the second delay time according to the amount of excitation energy applied to the laser medium by the excitation section. In this case, it is preferable that the excitation section includes a flash lamp as a light source, and the control section changes the set value of the first delay time or the second delay time according to a charging voltage of the flash lamp. The control section may have a first reference table in which the charging voltage and the set value of the first delay time or the second delay time are associated with each other, and may change the set value of the first delay time or the second delay time based on the first reference table. It is preferable that the excitation section includes an excitation light source, and the control section changes the set value of the first delay time or the second delay time according to the use duration of the excitation light source. The control section may have a second reference table in which the use duration and the set value of the first delay time or the second delay time are associated with each other, and may change the set value of the first delay time or the second delay time based on the second reference table.

In the laser device of the invention, it is preferable that the first resonator is constituted of a first mirror and a second mirror opposed to each other with the laser medium sandwiched therebetween, the second resonator is constituted of the first mirror and a third mirror opposed to the first mirror with the laser medium and the second mirror sandwiched therebetween, and the Q-value change unit is constituted of a first Q-value change section which is disposed on the common optical path, and a second Q-value change section which is disposed between the second mirror and the third mirror.

In this case, it is preferable that at least one of the first mirror, the second mirror, and the third mirror is movable along an optical axis direction, and in addition, it is preferable that the control section changes the set value of the first delay time according to the resonator length of the first resonator or changes the set value of the second delay time according to the resonator length of the second resonator. It is preferable that the control section has a third reference table in which the resonator length of the first resonator and the set value of the first delay time are associated with each other and/or a fourth reference table in which the resonator length of the second resonator and the set value of the second delay time are associated with each other, changes the set value of the first delay time based on the third reference table, and changes the set value of the second delay time based on the fourth reference table.

In the laser device of the invention, the control section switches the drive states of the first Q-value change section and the second Q-value change section among a first drive state where the Q values of the first resonator and the second resonator are in a low Q state lower than an oscillation threshold, a second drive state where the Q values of the first resonator and the second resonator are in a high Q state higher than the oscillation threshold, and a third drive state where the Q value of the first resonator is in the high Q state and the Q value of the second resonator is the low Q state. In this case, it is preferable that the control section brings the drive states of the first Q-value change section and the second Q-value change section into the first drive state at the time of the excitation of the laser medium. In addition, it is preferable that the control section switches the drive states of the first Q-value change section and the second Q-value change section from the first drive state to the third drive state in a case where the oscillation wavelength is the first wavelength after the excitation of the laser medium, and the control unit switches the drive states of the first Q-value change section and the second Q-value change section from the first drive state to the second drive state in a case where the oscillation wavelength is the second wavelength.

In the laser device of the invention, the first Q-value change section includes a first Q switch which changes the Q value of the first resonator according to an applied voltage, the second Q-value change section includes a second Q switch which changes the Q value of the second resonator according to an applied voltage, and the control section drives the first Q-value change section and the second Q-value change section by controlling the applied voltage.

A photoacoustic measurement device of the invention comprises the above-described laser device, and a probe which detects a photoacoustic wave generated in a subject using laser light emitted from the laser device.

It is preferable that the photoacoustic measurement device of the invention further comprises a signal processing section which processes a signal of the photoacoustic wave detected using the probe.

In the photoacoustic measurement device of the invention, it is preferable that the signal processing section has an acoustic image generation section which generates a photoacoustic image based on the signal of the photoacoustic wave, and it is preferable that the acoustic image generation section generates a reflected acoustic image based on a signal of a reflected wave of an acoustic wave transmitted to the subject.

The laser device and the photoacoustic measurement device of the invention comprise the solid-state laser medium which has the oscillation wavelengths at the first wavelength and the second wavelength with higher light emission efficiency than at the first wavelength, the excitation section, the first resonator which is a resonator oscillating light having the first wavelength and has the laser medium on the internal optical path, the second resonator which is a resonator oscillating light having the second wavelength and has the common optical path to the first resonator including the optical path, on which the laser medium is disposed, the Q-value change unit which includes at least the Q-value change section disposed on the common optical path and oscillates light having the first or second wavelength through Q switching, and the control section which controls the excitation section and the Q-value change unit. The control section controls the Q-value change unit to oscillate light having the first wavelength through Q switching when the first delay time has elapsed after the excitation of the laser medium has been started in a case where the oscillation wavelength is the first wavelength, and the control section controls the Q-value change unit to oscillate light having the second wavelength through Q switching when the second delay time, at which the intensity of light having the second wavelength is less than possible maximum intensity, has elapsed after the excitation of the laser medium has been started in a case where the oscillation wavelength is the second wavelength. With this, in a laser device which uses a laser medium with two oscillation wavelengths having different light emission efficiencies, it is possible to independently control the intensity of light at each wavelength without increasing the number of parts of the device.

BRIEF DESCRIPTION OF THE DRAWINGS

FIGS. 7A to 7E are timing charts showing the relationship between a delay time and the intensity of a laser light.

FIGS. 9A to 9D are timing charts relating to light emission of an excitation lamp, a voltage applied to a Q switch, and the output of a laser light.

DESCRIPTION OF THE PREFERRED EMBODIMENTS

Figure 1:
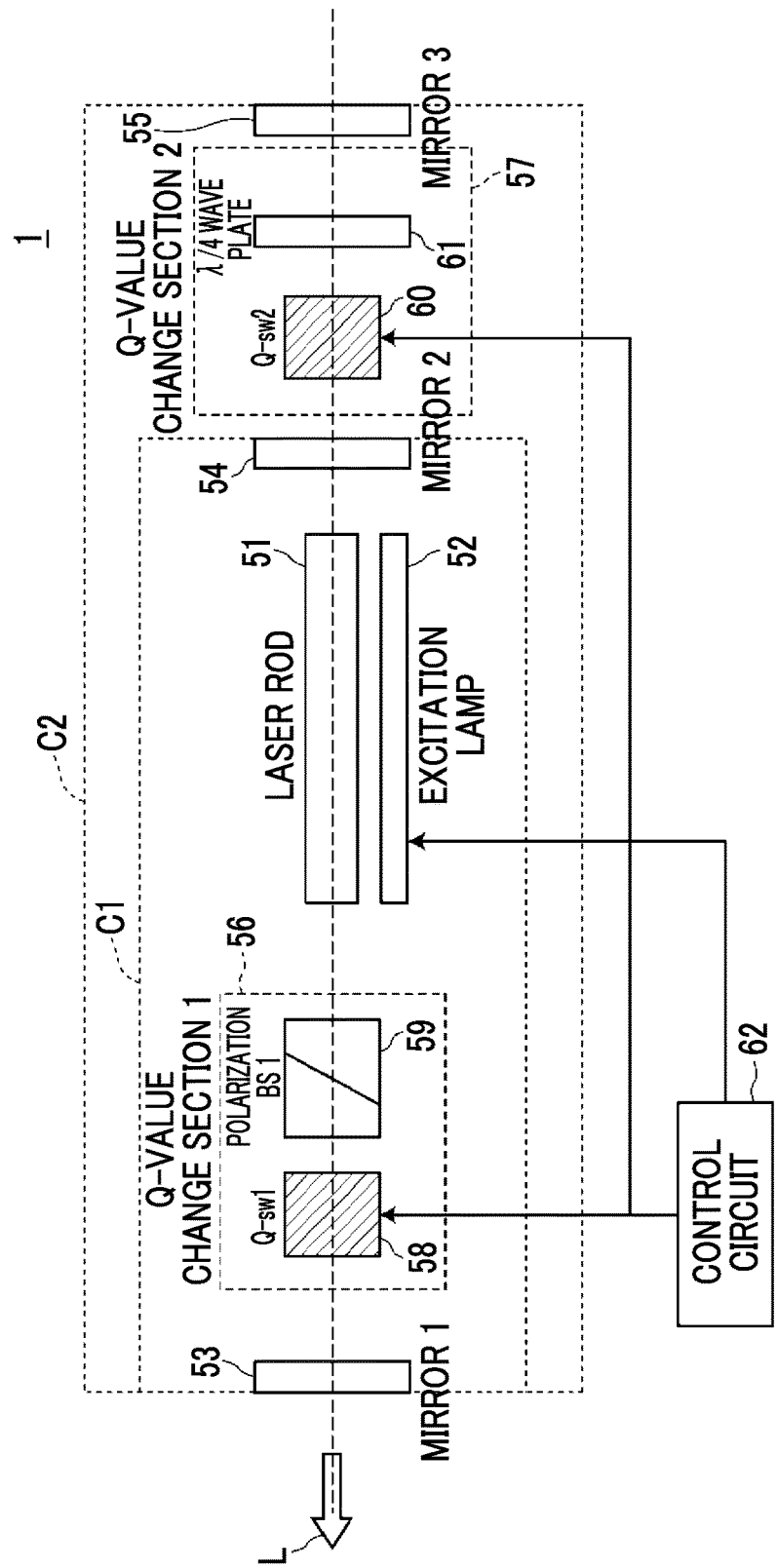
FIG. 1 is a schematic view showing the configuration of a laser device according to a first embodiment.

Hereinafter, although an embodiment of the invention will be described referring to the drawings, the invention is not limited to the embodiment, and the configurations may be combined with each other or subjected to various alterations unless such combinations or alterations depart from the spirit of the invention. For ease of visual recognition, the scale and the like of each of components in the drawings are made to be appropriately different from the actual scale and the like.

First Embodiment of Laser Device

A first embodiment of a laser device will be described. FIG. 1 is a schematic view showing the configuration of a laser device 1 according to this embodiment. As shown in FIG. 1, the laser device 1 has a laser rod 51, a flash lamp (excitation lamp) 52, a first mirror 53, a second mirror 54, a third mirror 55, a first Q-value change section 56, a second Q-value change section 57, and a control circuit 62. The first Q-value change section 56 and the second Q-value change section 57 corresponds to a Q-value change unit of the invention as a whole. The laser device 1 emits laser light L having a plurality of wavelength including a first wavelength and a second wavelength. For example, in this specification, it is assumed that a gain (light emission efficiency) at the second wavelength for laser oscillation is higher than a gain at the first wavelength.

The laser rod 51 is a laser medium. The laser rod 51 has oscillation wavelengths at 800 nm and 755 nm. For the laser rod 51, for example, alexandrite crystal is available. As described above, the gain of alexandrite for laser oscillation has a peak near the wavelength of 755 nm. The gain monotonously decreases when the wavelength becomes shorter in a wavelength range shorter than the wavelength of 755 nm. Furthermore, the gain monotonously decreases when the wavelength becomes longer in a wavelength range longer than the wavelength of 755 nm. The gain of alexandrite crystal at the wavelength of 800 nm is lower than the gain at the wavelength of 755 nm.

Figure 14:
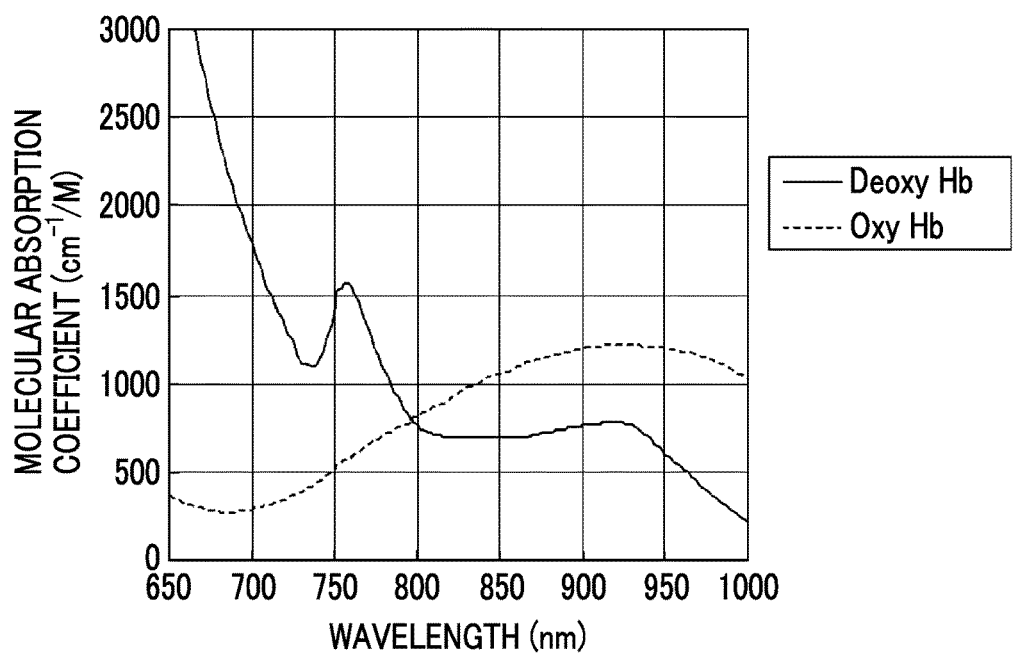
FIG. 14 is a graph showing molecular absorption coefficients for each optical wavelength of oxygenated hemoglobin and deoxygenated hemoglobin.
Figure 15:
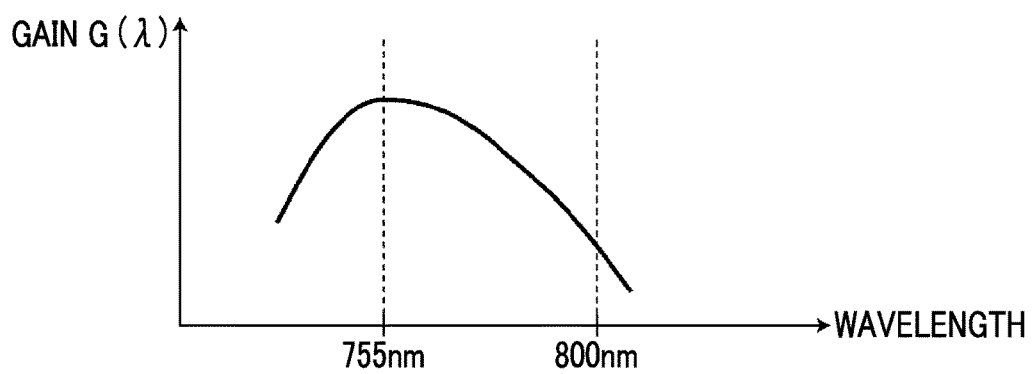
FIG. 15 is a graph showing a gain curve of alexandrite.

For example, about 800 nm is considered as the first wavelength (central wavelength), and about 755 nm is considered as the second wavelength. Referring to FIG. 14 described above, the molecular absorption coefficient at the wavelength of 755 nm of oxygenated hemoglobin contained in a large amount in the human artery is lower than the molecular absorption coefficient at the wavelength of 800 nm. The molecular absorption coefficient at the wavelength of 755 nm of deoxygenated hemoglobin contained in a large amount in the vein is higher than the molecular absorption coefficient at the wavelength of 800 nm. It is possible to distinguish between a photoacoustic signal from the artery and a photoacoustic signal from the vein by examining whether or not a photoacoustic signal obtained by irradiation with light having the wavelength of 755 nm is relatively greater or smaller than a photoacoustic signal obtained by irradiation with light having the wavelength of 800 nm by means of this property. Alternatively, oxygen saturation can be measured.

In regard to the selection of the first wavelength and the second wavelength, in theory, any combination of two wavelengths may be used insofar as there is a difference in optical absorption coefficient between two wavelengths to be selected, and the invention is not limited to the combination of about 755 nm and about 800 nm described above. If ease of handling is considered, it is preferable that two wavelengths to be selected are a combination of a wavelength of about 800 nm (accurately, 798 nm) at which the optical absorption coefficient becomes the same in oxygenated hemoglobin and deoxygenated hemoglobin and the wavelength of about 755 nm (accurately, 757 nm) at which the optical absorption coefficient of deoxygenated hemoglobin becomes a maximum value. In this case, the first wavelength does not need to be accurately 798 nm, and may be in a range of 793 nm to 802 nm, causing no problem in practical use. The second wavelength does not need to be accurately 757 nm, and may be, for example, in a range of 748 nm to 770 nm which is a half-width of a peak near the maximum value (757 nm), causing no problem in practical use.

The flash lamp 52 is an excitation light source as an excitation section of the invention, and irradiates the laser rod 51 with excitation light. The flash lamp 52 is intermittently driven. The flash lamp 52 is turned on interlocking with a flash lamp trigger transmitted from the control circuit 62. A light source other than the flash lamp 52 may be used as an excitation light source.

The first mirror 53, the second mirror 54, and the third mirror 55 are arranged on the optical axis of the laser rod 51. The first mirror 53 and the second mirror 54 are opposed to each other with the laser rod 51 sandwiched therebetween. The third mirror 55 is disposed on the opposite side to the laser rod 51 when viewed from the second mirror 54, and is opposed to the first mirror 53 with the laser rod 51 and the second mirror 54 sandwiched therebetween.

The first mirror 53 is an output mirror of light having the wavelength of 800 nm and light having the wavelength of 755 nm. The reflectivity to light having the wavelength of 800 nm of the first mirror 53 is higher than the reflectivity to light having the wavelength of 755 nm. For example, the reflectivity to light having the wavelength of 800 nm of the first mirror 53 is 80%, and the reflectivity to light having the wavelength of 755 nm is 70%. The reflectivity to light having the wavelength of 800 nm with a low gain is set to be high, whereby an oscillation (injection) energy threshold is reduced and the gain increases. With this, it is possible to shorten the pulse of pulse laser light.

The second mirror 54 reflects light having the wavelength of 800 nm and transmits light having the wavelength of 755 nm. For example, the reflectivity to light having the wavelength of 800 nm of the second mirror 54 is equal to or greater than 99.8%, and the reflectivity to light having the wavelength of 755 nm is equal to or less than 0.5%. The third mirror 55 reflects light having the wavelength of 755 nm. The reflectivity to light having the wavelength of 755 nm of the third mirror 55 is, for example, equal to or greater than 99.8%.

Of light emitted from the laser rod 51, light having the wavelength of 800 nm is reflected by the second mirror 54, and reciprocates between the first mirror 53 and the second mirror 54. The first mirror 53 and the second mirror 54 constitute a first resonator C1 which oscillates light having the wavelength of 800 nm. Light having the wavelength of 755 nm emitted from the laser rod 51 is transmitted through the second mirror 54, is reflected by the third mirror 55, and reciprocates between the first mirror 53 and the third mirror 55. The first mirror 53 and the third mirror 55 constitute a second resonator C2 which oscillates light having the wavelength of 755 nm. The resonator length of the first resonator C1 is shorter than the resonator length of the second resonator C2. An optical path from the first mirror 53 to the second mirror 54 is a common optical path for the first resonator C1 and the second resonator C2, and the laser rod 51 is disposed on the common optical path.

The first Q-value change section 56 is disposed on the common optical path of the first resonator C1 and the second resonator C2, and controls the Q values of the first resonator C1 and the second resonator C2. For example, the first Q-value change section 56 is disposed between the first mirror 53 and the laser rod 51. Instead of this, the first Q-value change section 56 may be disposed between the laser rod 51 and the second mirror 54. The first Q-value change section 56 includes a first Q switch 58 and a polarizer 59. The first Q switch 58 changes the Q values of the first resonator C1 and the second resonator C2 according to an applied voltage. For the first Q switch 58, an electro-optical element which changes the polarization state of light passing therethrough according to an applied voltage is available.

For the first Q switch 58, for example, a Pockels cell is used. The first Q switch 58 brings the first resonator C1 and the second resonator C2 into a low Q state when the applied voltage is a first voltage corresponding to Q switch off. The low Q state indicates a state where the Q value of the resonator is lower than a laser oscillation threshold. The first voltage is, for example, a voltage at which the first Q switch 58 functions as a quarter wave plate. The first Q switch 58 brings the first resonator C1 and the second resonator C2 into a high Q state when the applied voltage is a second voltage corresponding to Q switch on. The high Q state indicates a state where the Q value of the resonator is higher than the laser oscillation threshold. The absolute value of the second voltage is smaller than the absolute value of the first voltage, and the voltage may be a positive voltage or a negative voltage. The second voltage is, for example, 0 V (no voltage applied), and at this time, the polarization state of light transmitted through the first Q switch 58 is not changed. Since the Pockels cell serves as a quarter wave plate and the voltage changes depending on the wavelength, the second voltage corresponding to Q switch on is different between oscillation of the wavelength of 800 nm and oscillation of the wavelength of 755 nm. That is, the applied voltage to the Pockels cell is different between oscillation of the wavelength of 800 nm and oscillation of the wavelength of 755 nm. For this reason, compared to a configuration in which the applied voltage of 0 V to the Pockels cell corresponds to Q switch on, in other configurations, the control circuit of the Q switch or a control method thereof becomes slightly complicated. Accordingly, it is preferable that the first Q-value change section 56 has a configuration in which the applied voltage of 0 V corresponds to Q switch on.

The polarizer 59 is disposed between the laser rod 51 and the first Q switch 58. The polarizer 59 transmits only linearly polarized light in a predetermined direction. For the polarizer 59, for example, a beam splitter which transmits linearly polarized light (for example, p polarized light) in a predetermined direction and reflects a direction (for example, s polarized light) orthogonal to the predetermined direction is available. In a case where alexandrite crystal is used for the laser rod 51, or the like, if light emitted from the laser rod 51 is p polarized light, the polarizer 59 may be omitted.

Specifically, when the first voltage is applied to the first Q switch 58, the first Q switch 58 functions as a quarter wave plate. At this time, p polarized light incident on the first Q switch 58 from the polarizer 59 becomes circularly polarized light when passing through the first Q switch 58. Thereafter, light is reflected by the first mirror 53 and is incident on the first Q switch 58 in the opposite direction. Circularly polarized light incident on the first Q switch 58 in the opposite direction becomes s polarized light when passing through the first Q switch 58. Thereafter, light is reflected by the polarizer 59 which reflects s polarized light and is emitted outside the optical path of the resonator. When the applied voltage to the first Q switch 58 is 0 V (second voltage), p polarized light incident on the first Q switch 58 from the polarizer 59 is transmitted through the first Q switch 58 as p polarized light and is reflected by the first mirror 53. P polarized light reflected by the first mirror 53 is transmitted through the first Q switch 58 as p polarized light, is transmitted through the polarizer 59 which transmits p polarized light, and is incident on the laser rod 51.

The second Q-value change section 57 is disposed on the optical path of the second resonator C2 between the second mirror 54 and the third mirror 55, and controls the Q value of the second resonator C2. The second Q-value change section 57 includes a second Q switch 60 and a quarter wave plate 61. The second Q switch 60 changes the Q value of the second resonator C2 according to the applied voltage. For the second Q switch 60, an electro-optical element which changes the polarization state of light passing therethrough according to an applied voltage is available. The quarter wave plate 61 is disposed between the second Q switch 60 and the third mirror 55.

For the second Q switch 60, for example, a Pockels cell is used. The second Q switch 60 brings the second resonator C2 into a low Q state when the applied voltage is a third voltage corresponding to Q switch off. The third voltage is, for example, 0 V (no voltage applied), and at this time, the polarization state of light transmitted through the second Q switch 60 is not changed. The second Q switch 60 brings second resonator C2 into a high Q state when the applied voltage is a fourth voltage corresponding to Q switch on. The absolute value of the fourth voltage is greater than the absolute value of the third voltage, and the voltage may be a positive voltage or a negative voltage. The fourth voltage is, for example, a voltage at which the second Q switch 60 functions as a quarter wave plate.

Specifically, when the applied voltage to the second Q switch 60 is 0 V (third voltage), p polarized light incident on the second Q switch 60 from the laser rod 51 side through the second mirror 54 passes through the second Q switch 60 as p polarized light and becomes circularly polarized light when passing through the quarter wave plate 61, and circularly polarized light is reflected by the third mirror 55. Circularly polarized light reflected by the third mirror 55 becomes s polarized light when passing through the quarter wave plate 61 in the opposite direction, passes through second Q switch 60 as s polarized light, and returns to the laser rod 51. The second mirror 54 reflects light having the wavelength of 800 nm and transmits light having the wavelength of 755 nm. For this reason, light traveling between the second mirror 54 and the third mirror 55 is light having the wavelength of 755 nm, and light having the wavelength of 800 nm does not travel from the second mirror 54 to the third mirror 55 side. When the fourth voltage is applied to the second Q switch 60, the second Q switch 60 functions as a quarter wave plate. At this time, p polarized light incident on the second Q switch 60 from the laser rod 51 side through the second mirror 54 becomes circularly polarized light when passing through the second Q switch 60, and circularly polarized light also becomes s polarized light when passing through the quarter wave plate 61. Thereafter, light reflected by the third mirror 55 becomes circularly polarized light when passing through the quarter wave plate 61 in the opposite direction, circularly polarized light also becomes p polarized light when passing through the second Q switch 60, and p polarized light returns to the laser rod 51.

The control circuit 62 corresponds to a control section of the invention and drives the first Q-value change section 56 and the second Q-value change section 57. The control circuit 62 switches the drive states of the first resonator C1 and the second resonator C2 among a first drive state where both of the Q values of the respective resonators are brought into a low Q state lower than an oscillation threshold, a second drive state where both of the Q values of the respective resonators are brought into a high Q state higher than the oscillation threshold, and a third drive state where the first resonator C1 is brought into the high Q state and the second resonator C2 is brought into the low Q state. The control circuit 62 controls the applied voltage to the first Q switch 58 to drive the first Q-value change section 56 and controls the applied voltage to the second Q switch 60 to drive the second Q-value change section 57. The control circuit 62 transmits a Q switch trigger to the first Q-value change section and/or the second Q-value change section, and makes laser light be oscillated by means of the switching of the three drive states. The control circuit 62 also transmits a flash lamp trigger instructing to turn on the flash lamp 52 to drive the flash lamp 52.

In the first drive state, the first voltage is applied to the first Q switch 58, and the first Q switch 58 functions as a quarter wave plate. Furthermore, in the first drive state, the applied voltage to the second Q switch 60 is 0 V (third voltage), and the polarization state of light passing through the second Q switch 60 is not changed. Accordingly, the first Q switch 58 functions as a quarter wave plate, whereby light reflected by the first mirror 53 is not incident on the laser rod 51. Furthermore, the polarization state of light passing through the second Q switch 60 is not changed, whereby light having the wavelength of 755 nm reflected by the third mirror 55 is incident on the laser rod 51 as s polarized light. As a result, the first resonator C1 and the second resonator C2 are brought in the low Q state, and laser oscillation does not occur for both of the wavelength of 800 nm and the wavelength of 755 nm. The first Q switch 58 is disposed on the common optical path, and the first voltage is applied to the first Q switch 58, whereby the second resonator C2 can be brought into the low Q state. For this reason, in the first drive state, the applied voltage to the second Q switch 60 is not particularly to the third voltage, and the fourth voltage may be applied to the second Q switch 60 to make the second Q switch 60 function as a quarter wave plate.

In the second drive state, the applied voltage to the first Q switch 58 is 0 V (second voltage), and the polarization state of light passing through the first Q switch 58 is not changed. Furthermore, in the second drive state, the fourth voltage is applied to the second Q switch 60, and the second Q switch 60 functions as a quarter wave plate. Accordingly, the polarization state of light passing through the first Q switch 58 is not changed, whereby light reflected by the first mirror 53 is incident on the laser rod 51 as p polarized light. Furthermore, the second Q switch 60 functions as a quarter wave plate, whereby light having the wavelength of 755 nm reflected by the third mirror 55 is incident on the laser rod 51 as p polarized light. As a result, the first resonator C1 and the second resonator C2 are brought into the high Q state, and laser oscillation occurs. At the wavelength of 800 nm and the wavelength of 755 nm, since the gain at the wavelength of 755 nm is higher than the gain at the wavelength of 800 nm, the oscillation wavelength becomes 755 nm with a high gain.

In the third drive state, the applied voltage of the first Q switch 58 is 0 V (second voltage), and the polarization state of light passing through the first Q switch 58 is not changed. Furthermore, in the third drive state, the applied voltage of the second Q switch 60 is 0 V (third voltage), and the polarization state of light passing through the second Q switch 60 is not changed. The polarization state of light passing through the first Q switch 58 is not changed, whereby light reflected by the first mirror 53 is incident on the laser rod 51 as p polarized light. Furthermore, the polarization state of light passing through the second Q switch 60 is not changed, whereby light having the wavelength of 755 nm reflected by the third mirror 55 is incident on the laser rod 51 as s polarized light. As a result, the first resonator C1 is brought into the high Q state and the second resonator C2 is brought into the low Q state, and laser oscillation occurs in the first resonator C1. The first resonator C1 is a resonator having the wavelength of 800 nm, and the oscillation wavelength becomes 800 nm.

The control circuit 62 brings the drive states of the first Q-value change section 56 and the second Q-value change section 57 into the first drive state at the time of the excitation of the laser rod 51. That is, the flash lamp 52 is turned on when the first resonator C1 and the second resonator C2 are in the low Q state, and the excitation of the laser rod 51 is performed. The control circuit 62 switches the drive states of the first Q-value change section 56 and the second Q-value change section 57 from the first drive state to the third drive state in a case where the oscillation wavelength is 800 nm after the excitation of the laser rod 51. In the third drive state, since the first resonator C1 is in the high Q state and the second resonator C2 is in the low Q state, the oscillation wavelength becomes the wavelength of 800 nm. The Q value of the first resonator C1 is rapidly changed from the low Q state to the high Q state, whereby it is possible to obtain pulse laser light having the wavelength of 800 nm. That is, in order to realize Q switch oscillation of light by driving the first Q-value change section 56, in this case, a drive instruction to the first Q-value change section 56 by the control circuit 62 becomes a Q switch trigger.

The control circuit 62 switches the drive states of the first Q-value change section 56 and the second Q-value change section 57 from the first drive state to the second drive state in a case where the oscillation wavelength is 755 nm after the excitation of the laser rod 51. At this time, the control circuit 62 drives the second Q-value change section 57 such that the second resonator C2 is brought into the high Q state and drives the first Q-value change section 56 such that the first resonator is brought into the high Q state. Alternatively, the control circuit 62 may drive the second Q-value change section 57 such that the second resonator C2 is brought into the high Q state and then, may drive the first Q-value change section 56 such that the first resonator is brought into the high Q state. In the second drive state, while both resonators are brought into the high Q state, the oscillation wavelength becomes 755 nm with a high gain between the wavelength of 800 nm and the wavelength of 755 nm. The Q values of the first resonator and the second resonator C2 (in particular, the second resonator C2) are rapidly changed from the low Q state to the high Q state, whereby it is possible to obtain pulse laser light having the wavelength of 755 nm. That is, in order to realize Q switch oscillation of light by driving the second Q-value change section 57, in this case, a drive instruction to the second Q-value change section 57 by the control circuit 62 becomes a Q switch trigger.

The control circuit 62 has a delay time set for each wavelength in regard to the time (delay time) from the start of the excitation of the laser medium until Q switch oscillation of light, and oscillates light having each wavelength through Q switching according to each delay time. Specifically, the control circuit 62 controls the first Q-value change section 56 and the second Q-value change section 57 to oscillate light having the first wavelength through Q switching when a first delay time has elapsed after the excitation of the laser rod 51 has been started in a case where the oscillation wavelength is the first wavelength (in this embodiment, the wavelength of 800 nm), and controls the first Q-value change section 56 and the second Q-value change section 57 to oscillate light having the second wavelength through Q switching when a second delay time at which the intensity of light having the second wavelength is less than a possible maximum intensity (for example, 90%, 80%, or 50% of the possible maximum intensity) after the excitation of the laser rod 51 has been started in a case where the oscillation wavelength is the second wavelength (in this embodiment, the wavelength of 755 nm). The possible maximum intensity refers to the maximum intensity of light which is able to be output as potential capability in a case the laser medium is excited with certain excitation energy. In this way, the delay time is independently set for each wavelength, whereby it is possible to independently control the light intensity at each wavelength. Although the delay time is independently set for each wavelength, as a result, the delay time may have the same value. Detailed description of control for light intensity by the setting of the delay time will be described below.

Figure 2:
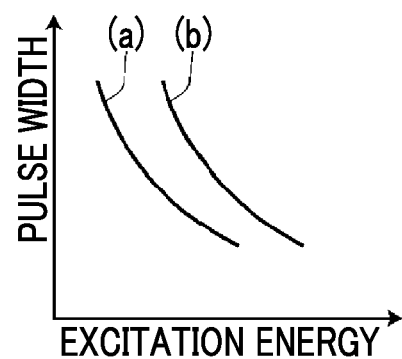
FIG. 2 is a graph showing the relationship between excitation energy and the pulse width of a laser light for each resonator length.

FIG. 2 is a graph showing the relationship between excitation energy and the pulse width of laser light for each resonator length. In the drawing, the relationship between excitation energy and the pulse width is shown for two resonator lengths. A graph (a) shows the relationship between excitation energy and the pulse width in a case where a resonator having a short resonator length is used, and a graph (b) shows the relationship between excitation energy and the pulse width in a case where a resonator having a long resonator length is used. Referring to the graph (a) and the graph (b), it is understood that, in a case where excitation energy is constant, it is possible to shorten the pulse width in a case where the resonator length is short compared to a case where the resonator length is long. In the laser device 1, since the first resonator C1 has the resonator length shorter than that of the second resonator C2, it is possible to make the pulse width of pulse laser light having the wavelength of 800 nm shorter than the pulse width of pulse laser light having the wavelength of 755 nm.

Figure 3:
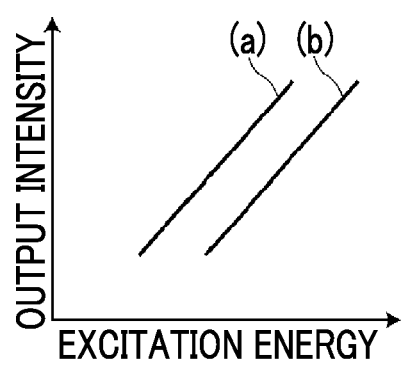
FIG. 3 is a graph showing the relationship between excitation energy and the intensity of a laser light for each resonator length.

FIG. 3 is a graph showing the relationship between excitation energy and the intensity of laser light for each resonator length. In the drawing, the relationship between excitation energy and the intensity of laser light is shown for two resonator lengths. A graph (a) shows the relationship between excitation energy and intensity in a case where a resonator having a short resonator length is used, and a graph (b) shows the relationship between excitation energy and intensity in a case where a resonator having a long resonator length is used. Referring to the graph (a) and the graph (b), it is understood that, in a case where excitation energy is constant, it is possible to increase a laser output in a case where the resonator length is short compared to a case where the resonator length is long. In the laser device 1, the first resonator C1 has the resonator length shorter than that of the second resonator C2, and it is possible to increase the laser output of light having the wavelength of 800 nm compared to a case where the resonator lengths of both resonators are the same.

Figure 4:
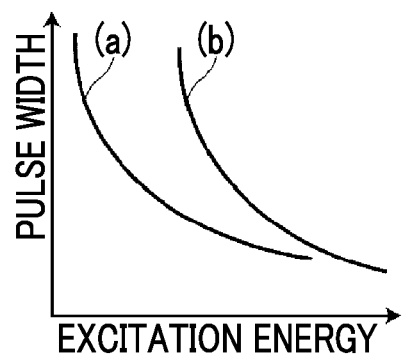
FIG. 4 is a graph showing the relationship between excitation energy and the pulse width of a laser light for each mirror reflectivity.

FIG. 4 is a graph showing the relationship between excitation energy and the pulse width of laser light for each mirror reflectivity. In the drawing, a graph (a) shows the relationship between excitation energy and the pulse width in a case where the reflectivity of the first mirror 53 as an output mirror is set to 80%, and a graph (b) shows the relationship between excitation energy and the pulse width in a case where the reflectivity of the first mirror 53 is set to 60%. Referring to the graph (a) and the graph (b), it is understood that, in a case where excitation energy is constant, it is possible to shorten the pulse width in a case where the reflectivity of the output mirror is high compared to a case where the reflectivity of the output mirror is low. The reflectivity to light having the wavelength of 800 nm of the first mirror 53 is higher than the reflectivity to light having the wavelength of 755 nm, whereby it is possible to make the pulse width of pulse laser light having the wavelength of 800 nm shorter than the pulse width of pulse laser light having the wavelength of 755 nm.

Figure 5:
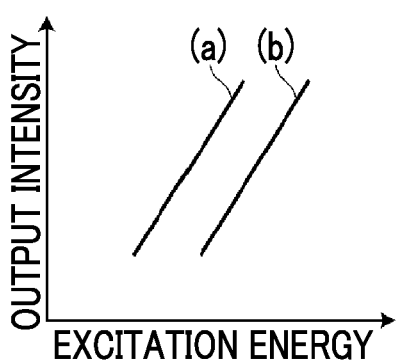
FIG. 5 is a graph showing the relationship between excitation energy and the intensity of a laser light for each mirror reflectivity.

FIG. 5 is a graph showing the relationship between excitation energy and the intensity of laser light for each mirror reflectivity. In the drawing, a graph (a) shows the relationship between excitation energy and intensity in a case where the reflectivity of the first mirror 53 is set to 80%, and a graph (b) shows the relationship between excitation energy and intensity in a case where the reflectivity of the first mirror 53 is set to 60%. Referring to the graph (a) and the graph (b), it is understood that, in a case where excitation energy is constant, it is possible to increase a laser output in a case where the reflectivity of the output mirror is high compared to a case where the reflectivity of the output mirror is low. The reflectivity to light having the wavelength of 800 nm of the first mirror 53 is higher than the reflectivity to light having the wavelength of 755 nm, whereby it is possible to increase the laser output of light having the wavelength of 800 nm compared to a case where the same reflectivity is set at both wavelengths.

Figure 6A:
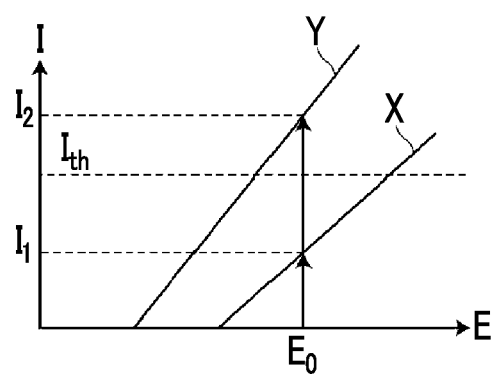
FIGS. 6A and 6B are graphs showing the relationship between excitation energy and the intensity of a laser light for each oscillation wavelength.
Figure 6B:
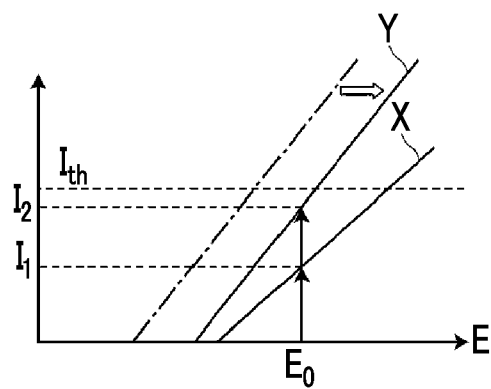

Control for light intensity by the setting of the delay time will be described. FIGS. 6A and 6B are graphs showing the relationship between excitation energy and the intensity of laser light for each oscillation wavelength. X in FIGS. 6A and 6B is a graph relating to light having the first wavelength with a low gain, and Y in FIGS. 6A and 6B is a graph relating to light having the second wavelength with a high gain. As shown in FIG. 6A, in a case of exciting the laser rod 51 with the same excitation energy $E_0$, if excitation energy is about to be increased in order to secure the intensity $I_1$ of desired light having the first wavelength, the intensity $I_2$ of light having the second wavelength may exceed a damage threshold $I_{th}$ of a lens, a mirror, or the like in the laser device 1. Accordingly, the inventors have found a method which reduces a gain of only light having the second wavelength by the setting of the delay time, and as shown in FIG. 6B, shifts the graph Y to the left. According to this method, it is possible to reduce the intensity $I_2$ of light having the second wavelength to be less than the damage threshold $I_{th}$ without reducing the intensity $I_1$ of light having the first wavelength.

Details are as follows. FIGS. 7A to 7E are timing charts showing the relationship between a delay time and the intensity of laser light. FIG. 7A shows the timing of the flash lamp (FL) trigger, FIG. 7B shows a temporal change in light emission intensity of the flash lamp, and FIG. 7C shows a temporal change in inverted distribution state density in the laser rod. FIG. 7D shows the timing of the Q switch (Qsw) trigger, and FIG. 7E shows pulse laser light which is output corresponding to each timing of the Q switch trigger. That is, FIGS. 7D and 7E shows that pulse laser light P1 is output in a case where the Q switch trigger is output at a timing T1 of a delay time D1, pulse laser light P2 is output in a case where the Q switch trigger is output at a timing T2 of a delay time D2, pulse laser light P3 is output in a case where the Q switch trigger is output at a timing T3 of a delay time D3, and pulse laser light P4 is output in a case where the Q switch trigger is output at a timing T4 of a delay time D4.

First, if the flash lamp trigger is transmitted from the control circuit 62, the flash lamp emits light interlocking with the flash lamp trigger. The light emission intensity of the flash lamp increases for a while after light emission, and if a peak is reached at a certain time, then, changes to decrease. In the laser rod which receives light from the flash lamp, since the inverted distribution is formed according to the amount of absorbed light, the state density of the inverted distribution increases with time, if a peak is reached at a certain time, then, gradually decreases, and subsequently, significantly decreases thereafter. That is, since the state density of the inverted distribution changes with time, the intensity of light at which laser oscillation is performed is different according to the timing at which the Q switch trigger is output. For example, in FIG. 7E, pulse laser light P2 having the maximum intensity is obtained at the timing T2 at which the inverted distribution state density is maximized, and the intensity (P1<P4<P3) of pulse laser light decreases at the timing at which the inverted distribution state density is small. That is, the delay time D2 is a delay time at which the intensity of light becomes the possible maximum intensity, and each of the delay times D1, D3, and D4 is a delay time at which the intensity of light becomes less than the possible maximum intensity. In general, the delay time D2 is about 150 µs to 200 µs, and in this embodiment, the time difference between adjacent Q switch triggers (that is, the difference between the delay times D1 and D2, the difference between the delay times D2 and D3, and the difference between the delay times D3 and D4) is, for example, tens of µs. In the description of FIGS. 7A to 7E described above, for simplification, although a case where the flash lamp and each Q-value change section respond instantaneously to the trigger from the control circuit 62 has been described, actually, a slight delay time (this is different from a delay time from excitation to oscillation) is present from the reception of the trigger until the response to the trigger. Accordingly, actually, it is necessary to output the flash lamp trigger and the Q switch trigger in consideration of the delay time from the reception of the trigger until the response to the trigger.

Figure 8A:
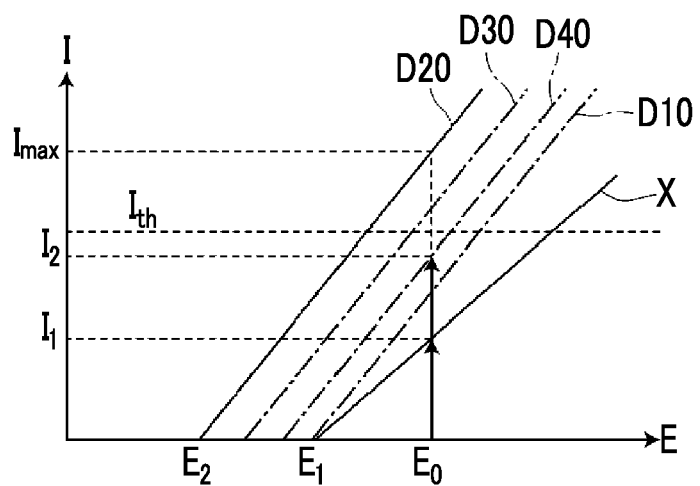
FIGS. 8A and 8B are graphs showing a manner in which the relationship between excitation energy and the intensity of a laser light changes according to a delay time.
Figure 8B:
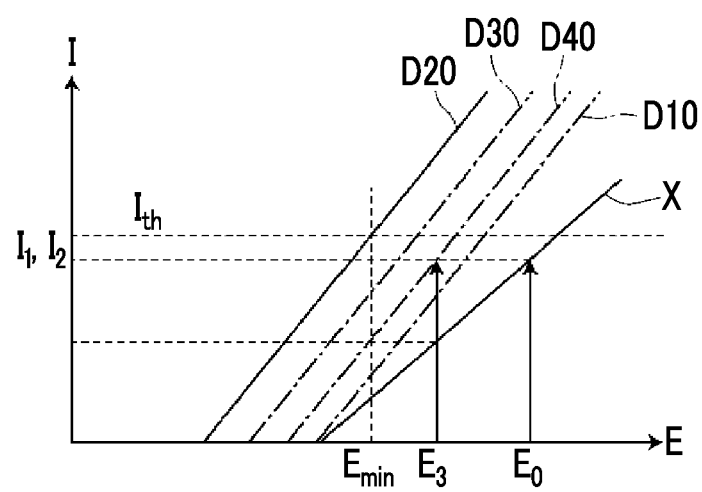

FIGS. 8A and 8B are graphs showing a manner in which the relationship between excitation energy and the intensity of laser light changes according to the delay time. In FIGS. 8A and 8B, D10 to D40 are graphs showing the intensity of light having the second wavelength, and X is a graph showing the intensity of light having the first wavelength. Specifically, D10 is a graph showing the intensity of light at the delay time D1, D20 is a graph showing the intensity of light at the delay time D2, D30 is a graph showing the intensity of light at the delay time D3, and D40 is a graph showing the intensity of light at the delay time D4. The graph of D20 is a graph which applies a maximum intensity $I_{max}$ for each excitation energy. As will be apparent from FIG. 8A, for example, the Q switch trigger is output at the timing of the delay time D4 or D1, whereby it is possible to suppress the intensity $I_2$ of light having the second wavelength in a range of less than the possible maximum intensity and to further reduce the intensity $I_2$ of light having the second wavelength to be less than the damage threshold $I_{th}$. In this embodiment, in order to enable wavelength switching, the second wavelength should constantly have a higher gain than the first wavelength. Accordingly, the delay time is set such that an oscillation threshold excitation energy $E_2$ relating to the second wavelength is smaller than an oscillation threshold excitation energy $E_1$ relating to the first wavelength.

For example, as in FIG. 8B, even if the intensities of light at each wavelength are arranged, since there is a lower limit $E_{min}$ to excitation energy, in a typical setting (for example, the delay time D2), the intensities of light at each wavelength may not be arranged only by reducing excitation energy. Accordingly, even in such a case, for example, if the setting of the delay time is changed from D2 to D4, it is possible to make the intensities $I_1$ and $I_2$ at each wavelength equal with excitation energy $E_3$ and $E_0$ equal to or greater than $E_{min}$. In this specification, when the intensities of light at each wavelength are arranged or equal, this refers that the intensity difference of light at each wavelength is within 10% based on the intensity of light having the first wavelength. In the above description, although a case where the setting of the delay time relating to oscillation of light having the second wavelength is changed has been described, the setting of the delay time relating to oscillation of light having the first wavelength may be changed.

Hereinafter, the operation of the Q-value change section and switching between the oscillation wavelengths will be described referring to FIGS. 9A to 9D. FIGS. 9A to 9D are timing charts relating to light emission of an excitation lamp, a voltage applied to a Q switch, and the output of laser light. The control circuit 62 transmits the flash lamp (excitation lamp) trigger to turn on the flash lamp 52 at the time t1 (FIG. 9A). The control circuit 62 applies the first voltage to the first Q switch 58 (Q-sw1) before the flash lamp 52 is turned on (FIG. 9B), and sets the applied voltage to the second Q switch 60 (Q-sw2) to 0 V (third voltage) (FIG. 9C). The time at which the first voltage is applied to the first Q switch 58 may be the time slightly before the time t1. Alternatively, the first voltage may be continued to be applied to the first Q switch 58 from previous pulse laser light emission. The first voltage is applied to the first Q switch 58, whereby the first Q switch 58 functions as a quarter wave plate. Voltage application to the second Q switch 60 is not performed, whereby the polarization state of light passing through the second Q switch 60 is not changed.

If the laser rod 51 is excited at the time t1, p polarized light is emitted from the laser rod 51. However, light emitted from the laser rod 51 toward the first mirror 53 reciprocates the first Q switch 58 which functions as a quarter wave plate, has the polarization direction rotated by 90°, is unable to pass through the polarizer 59, and does not return to the laser rod 51. Of light emitted from the laser rod 51 toward the second mirror 54, light having the wavelength of 755 nm reciprocates the quarter wave plate 61 and has the polarization direction rotated by 90°; thus, light having the wavelength of 755 nm does not contribute to the laser oscillation of the laser rod 51 having a predetermined polarization axis. Accordingly, the Q values of the first resonator C1 and the second resonator C2 are brought into the low Q state, and the first resonator C1 and the second resonator C2 do not oscillate.

The control circuit 62 transmits an instruction to change the applied voltage of the first Q switch 58 as a Q switch trigger and changes the applied voltage of the first Q switch 58 from the first voltage to 0 V (second voltage) at the time t2 after a delay time Dx from the time t1 (FIG. 9B). At this time, the control circuit 62 keeps the applied voltage of the second Q switch 60 at 0 V (FIG. 9C). The applied voltage of the first Q switch 58 is changed to 0 V, whereby the Q value of the first resonator C1 changes from the low Q state to the high Q state. The Q value of the second resonator C2 is maintained in the low Q state. Only the first resonator C1 is brought into the high Q state, whereby laser oscillation occurs at the wavelength of 800 nm and pulse laser light having the wavelength of 800 nm is emitted from the first mirror 53 (FIG. 9D). The delay time Dx is a delay time set for oscillation of light having the wavelength of 800 nm, and is set, for example, such that the intensity of light having the wavelength of 800 nm with a low gain becomes the possible maximum intensity.

The control circuit 62 transmits the flash lamp trigger after the emission of pulse laser light having the wavelength of 800 nm to turn on the flash lamp 52 at the time t3 (FIG. 9A). The control circuit 62 applies the first voltage to the first Q switch 58 at the time before the time t3 (FIG. 9B), and the Q values of the first resonator C1 and the second resonator C2 are brought into the low Q state. The control circuit 62 changes the applied voltage of the first Q switch 58 from the first voltage to 0 V and changes the applied voltage of the second Q switch 60 from 0 V to the fourth voltage at the time t4 after a delay time Dy from the time t3. If the applied voltage of the first Q switch 58 and the applied voltage of the second Q switch 60 are changed simultaneously or the applied voltage of the second Q switch 60 is first changed and the applied voltage of the first Q switch 58 is changed subsequently, laser oscillation occurs at the wavelength of 755 nm with a high gain between the wavelength of 800 nm and the wavelength of 755 nm, and pulse laser light having the wavelength of 755 nm is emitted from the first mirror 53 (FIG. 9D). The delay time Dy is a delay time set independently from the delay time Dx for oscillation of light having the wavelength of 755 nm, and is set, for example, such that the intensity of light having the wavelength of 755 nm with a high gain is less than the possible maximum intensity and becomes equal to the intensity of light having the wavelength of 800 nm.

The first Q-value change section 56 and the second Q-value change section 57 may be switched among the first, second, and third drive states, and the specific configurations of the first Q-value change section 56 and the second Q-value change section 57 are not limited to those described above. For example, the first Q-value change section 56 may have a configuration in which a Pockels cell and a quarter wave plate are combined like the second Q-value change section 57, or the second Q-value change section 57 may have a configuration in which a Pockels cell and a polarizer are combined like the first Q-value change section 56.

The control circuit 62 can have a configuration in which the set value of each delay time set according to the amount of excitation energy applied to the laser rod 51 by the flash lamp 52 or regarding oscillation of light having the first wavelength or the second wavelength is automatically changed. With this, for example, in a case where the target intensity of light to be output is determined, excitation energy should be changed, or in a case where excitation energy is not stable, if the control circuit 62 changes the set value of the delay time so as to cancel change in excitation energy, it becomes easy to maintain the target intensity. For example, in a case where the excitation light source is the flash lamp 52, the control circuit 62 can change the set value of each delay time according to the charging voltage of the flash lamp based on the relationship between the charging voltage of the flash lamp 52 and the amount of excitation energy. In this case, the control circuit 62 may have a reference table (first reference table) in which the charging voltage and the set value (or the amount of change) of the first or second delay time are associated with each other, or a relational expression in which the charging voltage and the set value of the first or second delay time are related to each other. For example, the control circuit 62 measures the charging voltage or reads the set value of the charging voltage to acquire the value of the charging voltage, reads the set value (the amount of change) of the first or second delay time corresponding to the acquire charging voltage with reference to the first reference table, and newly sets the read set value to a first or second delay time (or applies the read amount of change to the set value of the first or second delay time). The control circuit 62 may change the set value of each delay time according to the use duration of the excitation light source based on the relationship between the use duration (including the use time) of the excitation light source, such as the flash lamp 52, and the amount of excitation energy. In this case, the control circuit 62 may have a reference table (second reference table) in which the use duration and the set value (or the amount of change) of the first or second delay time are associated with each other, or may have a relational expression in which the use duration and the set value (or the amount of change) of the first or second delay time are related to each other. For example, the control circuit 62 measures the use duration to acquire the length of the use duration, reads the set value (or the amount of change) of the first or second delay time corresponding to the acquired use duration with reference to the second reference table, and newly the read set value to a first or second delay time (or applies the read amount of change to the set value of the first or second delay time).

At least one of the first mirror 53, the second mirror 54, and the third mirror 55 may be made movable in the optical axis direction. At least one of the three mirrors is made movable in the optical axis direction, whereby the relative interval between the mirrors is adjustable and the resonator length of the first resonator C1 or the resonator length of the second resonator C2 is changeable. At least one of the resonator length of the first resonator C1 and the resonator length of the second resonator C2 is changed, whereby it is possible to change at least one of the pulse width of pulse laser light having the wavelength of 800 nm and the pulse width of pulse laser light having the wavelength of 755 nm. With this structure, for example, change in pulse width with the reflectivity of the mirror may be corrected. In this case, the control circuit 62 may have a reference table (third reference table) in which the resonator length of the first resonator C1 and the set value (or the amount of change) of the delay time Dx are associated with each other and/or a reference table (fourth reference table) in which the resonator length of the second resonator C2 and the set value (or the amount of change) of the delay time Dy are associated with each other, or may have a relational expression in which the resonator length and the set value of the delay time are related to each other. For example, the control circuit 62 acquires the resonator length of each resonator from the amount of movement of each mirror, reads the set value (the amount of change) of the first or second delay time corresponding to the acquired resonator length with reference to the third reference table and/or fourth reference table, and newly sets the read set value to a first or second delay time (or applies the read amount of change to the set value of the first or second delay time).

As described above, the laser device 1 of this embodiment comprises a solid-state laser medium (laser rod 51) which has oscillation wavelengths at the first wavelength (800 nm) and the second wavelength (755 nm) with higher light emission efficiency than at the first wavelength, an excitation section (flash lamp 52), the first resonator C1 which is a rotator oscillating light having the first wavelength and has the laser medium on an internal optical path, the second resonator C2 which is a resonator oscillating light having the second wavelength and has a common optical path for the first resonator including an optical path, on which the laser medium is disposed, a Q-value change unit (first Q-value change section 56 and second Q-value change section 57) which includes at least a Q-value change section disposed on the common optical path and oscillates light having the first or second wavelength through Q switching, and a control section (control circuit 62) which controls the excitation section and the Q-value change unit. The control section controls the Q-value change unit to oscillate light having the first wavelength through Q switching when a first delay time has elapsed after the excitation of the laser medium has been started in a case where the oscillation wavelength is the first wavelength, and the control section controls the Q-value change unit to oscillate light having the second wavelength through Q switching when a second delay time, at which the intensity of light having the second wavelength is less than possible maximum intensity, has elapsed after the excitation of the laser medium has been started in a case where the oscillation wavelength is the second wavelength. That is, in the laser device 1, the delay time Dx for oscillating light having the first wavelength and the delay time Dy for oscillating light having the second wavelength are set independently from each other. With this, in a laser device which uses a laser medium having two oscillation wavelengths with different light emission efficiencies, it is possible to independently control the intensity of light at each wavelength by adjusting the delay times without increasing the number of parts of the device.

In this embodiment, the first mirror 53 and the second mirror 54 constitute the first resonator C1 which oscillates light having the wavelength of 800 nm, and the first mirror 53 and the third mirror 55 constitute the second resonator C2 which oscillates light having the wavelength of 755 nm. The laser rod 51 has the oscillation wavelengths at the wavelength of 800 nm and the wavelength of 755 nm, and light emission efficiency at the wavelength of 755 nm is higher than light emission efficiency at the wavelength of 800 nm. The first Q-value change section 56 is disposed in a common portion for the first resonator C1 and the second resonator C2, and the second Q-value change section 57 is disposed between the second mirror 54 and the third mirror 55. It is possible to control the Q values of the first resonator C1 and the second resonator C2 by driving the first Q-value change section 56. Furthermore, it is possible to control only the Q value of the second resonator C2 by driving the second Q-value change section 57.

In this embodiment, the first Q switch 58 is inserted into the first resonator C1 for the wavelength of 800 nm with a low gain. The first Q switch 58 and the second Q switch 60 are inserted into the second resonator C2 for the wavelength of 755 nm with a high gain. In JP2013-089680A, two Pockels cells are inserted into the resonators having both wavelengths, and in particular, there is a problem in that output is lowered at the wavelength of 800 nm with a low gain. In this embodiment, since the number of Pockels cells inserted into the first resonator C1 may be one, and it is not necessary to dispose a plurality of elements, which change the polarization state of light, in the first resonator C1, in particular, it is possible to suppress lowering of laser output with the insertion of a plurality of Pockels cells for the wavelength of 800 nm with low laser output.

In this embodiment, the first resonator C1 and the second resonator C2 are constituted on one axis such that the optical axes of light having the wavelength of 800 nm and light having the wavelength of 755 nm become parallel. With this, it is possible to use an optical member, such as a mirror or a Q-value change section, in common for light having the wavelength of 800 nm and light having the wavelength of 755 nm. In addition, in this embodiment, the third mirror 55 is disposed far from the second mirror 54 when viewed from the laser rod 51, and the resonator length of the first resonator C1 is shorter than the resonator length of the second resonator C2. The resonator length of the first resonator C1 is made short, whereby it is possible to shorten the pulse of pulse laser light at the wavelength of 800 nm with a low gain.

Second Embodiment of Laser Device

Figure 10:
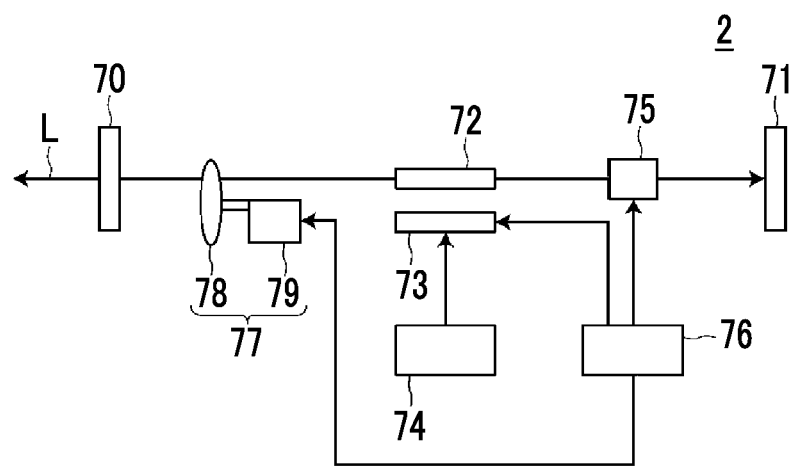
FIG. 10 is a schematic view showing the configuration of a laser device according to a second embodiment.

Next, a second embodiment of a laser device will be described. FIG. 10 is a schematic view showing the configuration of a laser device 2 according to the second embodiment. The laser device 2 of this embodiment has a wavelength selection section which is provided in a resonator and includes a plurality of band pass filters having different transmission wavelengths, and selects an oscillation wavelength using the wavelength selection section.

Specifically, the laser device 2 has two mirrors 70 and 71 constituting a resonator, a laser rod 72, a flash lamp 73, a power supply circuit 74, a Q switch 75, a control circuit 76, and a wavelength selection section 77. The laser rod 72 is a laser medium, and as in the first embodiment, for example, alexandrite crystal can be used as the laser rod 72. In this embodiment, for example, a first wavelength with a low gain is 800 nm, and a second wavelength with a high gain is 755 nm. The flash lamp 73 is an excitation light source to which the power supply circuit 74 is connected, and irradiates the laser rod 72 with excitation light. A light source other than the flash lamp 73 may be used as an excitation light source.

The mirrors 70 and 71 are opposed to each other with the laser rod 72 sandwiched therebetween, and a resonator is constituted of the mirrors. In this embodiment, the resonator corresponds to both of the first and second wavelengths. That is, the resonator oscillates light having both of the first and second wavelengths. For example, the mirror 70 is an output side. The Q switch 75 and the wavelength selection section 77 are disposed on an optical path in the resonator. The Q value of the resonator is changed by the Q switch 75. As the Q switch, for example, a Pockels cell is available.

The wavelength selection section 77 is used for switching the oscillation wavelength between the first wavelength and the second wavelength. The wavelength selection section 77 includes a plurality of band pass filters (BPF) 78 which have different transmission wavelengths and a drive section 79 which rotationally drives the band pass filters 78. The wavelength selection section 77 selectively inserts a specific band pass filter among a plurality of band pass filters 78 on the optical path of the resonator. The wavelength selection section 77 includes, for example, a first band pass filter which transmits light having a central wavelength of 755 nm, and a second band pass filter which transmits light having a central wavelength of 800 nm. The first and second band pass filters are constituted by rotors which are disposed into an angle range of 0° to 180° and an angle range of 180° to 360°, and are constituted such that light to be transmitted therethrough is changed according to rotational displacement. With this, the first band pass filter is inserted on the optical path of the resonator while rotating the rotors to set the oscillation wavelength to 755 nm, and the second band pass filter is inserted on the optical path of the resonator to set the oscillation wavelength to 800 nm.

The drive section 79 rotationally drives a plurality of band pass filters 78 constituted of rotors such that the band pass filter inserted on the optical path of the resonator is sequentially switched. A rotation state regarding a band pass filter on the optical path is detected by, for example, a rotary encoder (not shown).

The control circuit 76 transmits the flash lamp trigger for controlling light emission of the flash lamp 73, and makes the flash lamp 73 irradiate the laser rod 72 with excitation light. The control circuit 76 monitors the state of the BPF and transmits the flash lamp trigger based on the state. For example, the control circuit 76 transmits the flash lamp trigger if the state of the BPF is at a position obtained by subtracting the amount of displacement of the rotor for the delay time from the excitation of the laser medium until Q switch oscillation from the drive position of the rotor where the band pass filter corresponding to the wavelength of light to be emitted is inserted on the optical path. The delay time is set for each wavelength of light to be emitted. For example, the delay time for the wavelength of 800 nm is set such that the intensity of light becomes the possible maximum intensity, and the delay time for the wavelength of 755 nm is set such that the intensity of light becomes less than the possible maximum intensity. The control circuit 76 transmits the Q switch trigger to the Q switch 75 when the delay time set for each wavelength of light to be emitted has elapsed after the transmission of the flash lamp trigger. The Q switch 75 rapidly changes the resonator from the low Q state to the high Q state in response to the Q switch trigger (the Q switch is turned on), whereby light is output from the mirror 70 on the output side.

As described above, the laser device 2 of this embodiment comprises a solid-state laser medium (laser rod 72) which has oscillation wavelengths at the first wavelength (800 nm) and the second wavelength (755 nm) with higher light emission efficiency that at the first wavelength, an excitation section (flash lamp 73), a first resonator (mirrors 70 and 71) which is a resonator oscillating light having the first wavelength and has the laser medium on an internal optical path, a second resonator (mirrors 70 and 71) which is a resonator oscillating light having the second wavelength and has a common optical path for the first resonator including an optical path, on which the laser medium is disposed, a Q-value change unit (Q switch 75) which includes at least a Q-value change section disposed on the common optical path and oscillates light having the first or second wavelength through Q switching, and a control section (control circuit 76) which controls the excitation section and the Q-value change unit. The control section controls the Q-value change unit to oscillate light having the first wavelength through Q switching when a first delay time has elapsed after the excitation of the laser medium has been started in a case where the oscillation wavelength is the first wavelength, and the control section controls the Q-value change unit to oscillate light having the second wavelength through Q switching when a second delay time, at which the intensity of light having the second wavelength is less than possible maximum intensity, has elapsed after the excitation of the laser medium has been started in a case where the oscillation wavelength is the second wavelength. That is, in the laser device 2, the delay time for oscillating light having the first wavelength and the delay time for oscillating light having the second wavelength are set independently from each other. With this, in a laser device which uses a laser medium having two oscillation wavelengths with different light emission efficiencies, it is possible to independently control the intensity of light at each wavelength by adjusting the delay times without increasing the number of parts of the device.

Third Embodiment of Laser Device

Figure 11:
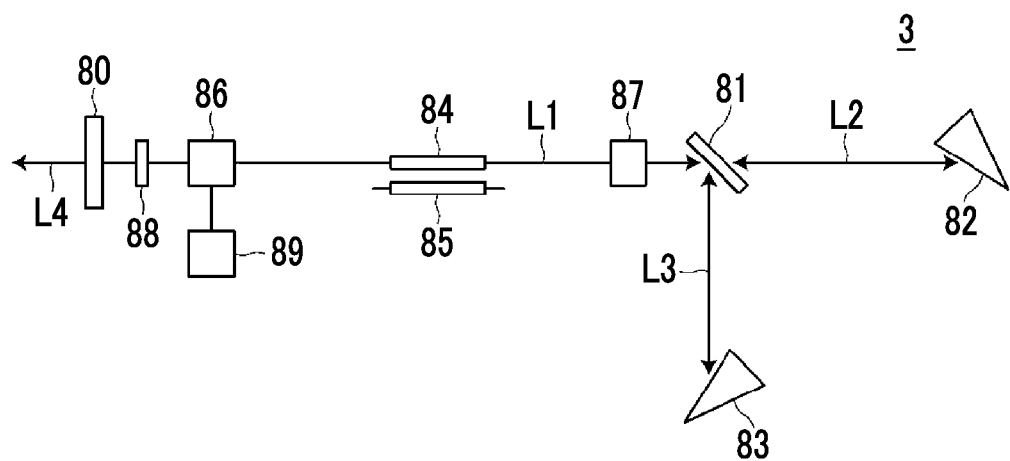
FIG. 11 is a schematic view showing the configuration of a laser device according to a third embodiment.

Next, a third embodiment of a laser device will be described. FIG. 11 is a schematic view showing the configuration of a laser device 3 according to the third embodiment. The laser device 3 of the embodiment performs oscillation at a plurality of wavelengths using a branching polarizer and a resonance optical path selection section.

Specifically, the laser device 3 has an output-side mirror 80, a polarizer 81, a first reflection prism 82, a second reflection prism 83, a laser rod 84, a flash lamp 85, two Pockels cells 86 and 87, a λ/4 wave plate 88, and a trigger control section 89.

The laser rod 84 and the flash lamp 85 are disposed between the mirror 80 and the polarizer 81. The laser rod 84 is a laser medium, and as in the first embodiment, for example, alexandrite crystal can be used as the laser rod 84. In this embodiment, for example, the first wavelength with a low gain is 800 nm, and the second wavelength with a high gain is 755 nm. The flash lamp 85 is an excitation light source, and irradiates the laser rod 84 with excitation light interlocking with the flash lamp trigger transmitted from the control circuit 89. A light source other than the flash lamp 85 may be used as an excitation light source.

The Pockels cell 87 which constitutes a resonance optical path selection section is disposed between the laser rod 84 and the polarizer 81. A voltage which rotates the polarization direction of incident linearly polarized light by 90° when oscillating the wavelength of 800 nm is applied to the Pockels cell 87, and no voltage is applied when oscillating the wavelength of 755 nm. The polarizer 81 which is an optical path branch section transmits p polarized light and reflects s polarized light. Light transmitted through the polarizer 81 travels along a first branch optical path L2 and is reflected by the first reflection prism 82. Light reflected by the polarizer 81 travels along a second branch optical path L3 and is reflected by the second reflection prism 83.

The first reflection prism 82 is disposed so as to become a Brewster angle with respect to incident light. The first reflection prism 82 has a dielectric reflection film which selectively reflects light having the wavelength of 755 nm. The second reflection prism 83 has a dielectric reflection film which selectively reflects light having the wavelength of 800 nm. The resonator (first resonator) of the wavelength of 800 nm is constituted of the mirror 80 and the second reflection prism 83. The resonator (second resonator) of the wavelength of 755 nm is constituted of the mirror 80 and the first reflection prism 82. The resonators have a common optical path L1.

A Q switch which is constituted of the Pockels cell 86 and the λ/4 wave plate 88 is also disposed on the common optical path L1. The applied voltage of the Pockels cell 86 is controlled by the control circuit 89. When the flash lamp 85 is turned on, no voltage is applied to the Pockels cell 86 constituting the Q switch, and the Q switch is turned off. The Q switch is turned on when a predetermined delay time has elapsed after the flash lamp 85 has been turned on. With this, laser oscillation occurs in the first resonator or the second resonator according to the state of the Pockels cell 87, and light is output from the mirror 80. The delay time is set for each wavelength of light to be emitted. For example, the delay time for the wavelength of 800 nm is set such that the intensity of light becomes the possible maximum intensity, and the delay time for the wavelength of 755 nm is set such that the intensity of light becomes less than the possible maximum intensity.

In a case where no voltage is applied to the Pockels cell 87 constituting the resonance optical path selection section, p polarized light emitted from the laser rod 84 is transmitted through the Pockels cell 87 as p polarized light, is transmitted through the polarizer 81 which transmits p polarized light, passes through the first branch optical path L2, and is reflected by the first reflection prism 82. Light reflected by the first reflection prism 82 passes through the polarizer 81 and the Pockels cell 87 in the opposite direction as p polarized light and is incident on the laser rod 84, laser oscillation occurs, and laser light L4 is output. The first reflection prism 82 selectively reflects light having the wavelength of 755 nm, whereby light having the wavelength of 755 nm is oscillated.

In a case where a voltage which rotates the polarization direction of incident light by 90° is applied to the Pockels cell 87, p polarized light emitted from the laser rod 84 has the polarization direction rotated by 90° when transmitted through the Pockels cell 87, and becomes s polarized light. Light which becomes s polarized light is reflected by the polarizer 81, passes through the second branch optical path L3, and is reflected by the second reflection prism 83. Light reflected by the second reflection prism 83 passes through the polarizer 81 in the opposite direction and is incident on the Pockels cell 87 in the opposite direction. Light incident on the Pockels cell 87 as s polarized light has the polarization direction rotated by 90° when passing through the Pockels cell 87, becomes p polarized light, and is incident on the laser rod 84, laser oscillation occurs, and laser light L4 is output. The second reflection prism 83 selectively reflects light having the wavelength of 800 nm, whereby light having the wavelength of 800 nm is oscillated.

As described above, the laser device 3 of this embodiment comprises a solid-state laser medium ((laser rod 84) which has oscillation wavelengths at the first wavelength (800 nm) and the second wavelength (755 nm) with higher light emission efficiency than at the first wavelength, an excitation section (flash lamp 85), a first resonator (mirror 80 and reflection prism 83) which is a resonator oscillating light having the first wavelength and has the laser medium on an internal optical path, a second resonator (mirror 80 and reflection prism 82) which is a resonator oscillating light having the second wavelength and has a common optical path for the first resonator including an optical path, on which the laser medium is disposed, a Q-value change unit (Pockels cells 86) which includes at least a Q-value change section disposed on the common optical path and oscillates light having the first or second wavelength through Q switching, and a control section (control circuit 89) which controls the excitation section and the Q-value change unit. The control section controls the Q-value change unit to oscillate light having the first wavelength through Q switching when a first delay time has elapsed after the excitation of the laser medium has been started in a case where the oscillation wavelength is the first wavelength, and the control section controls the Q-value change unit to oscillate light having the second wavelength through Q switching when a second delay time, at which the intensity of light having the second wavelength is less than possible maximum intensity, has elapsed after the excitation of the laser medium has been started in a case where the oscillation wavelength is the second wavelength. That is, in the laser device 3, the delay time for oscillating light having the first wavelength and the delay time for oscillating light having the second wavelength are set independently from each other. With this, in a laser device which uses a laser medium having two oscillation wavelengths with different light emission efficiencies, it is possible to independently control the intensity of light at each wavelength by adjusting the delay times without increasing the number of parts of the device.

In the second and third embodiments, the control section can have a configuration in which the set value of each delay time set according to the amount of excitation energy or the resonator length or regarding oscillation light having the first wavelength or the second wavelength.

Embodiment of Photoacoustic Measurement Device

Figure 12:
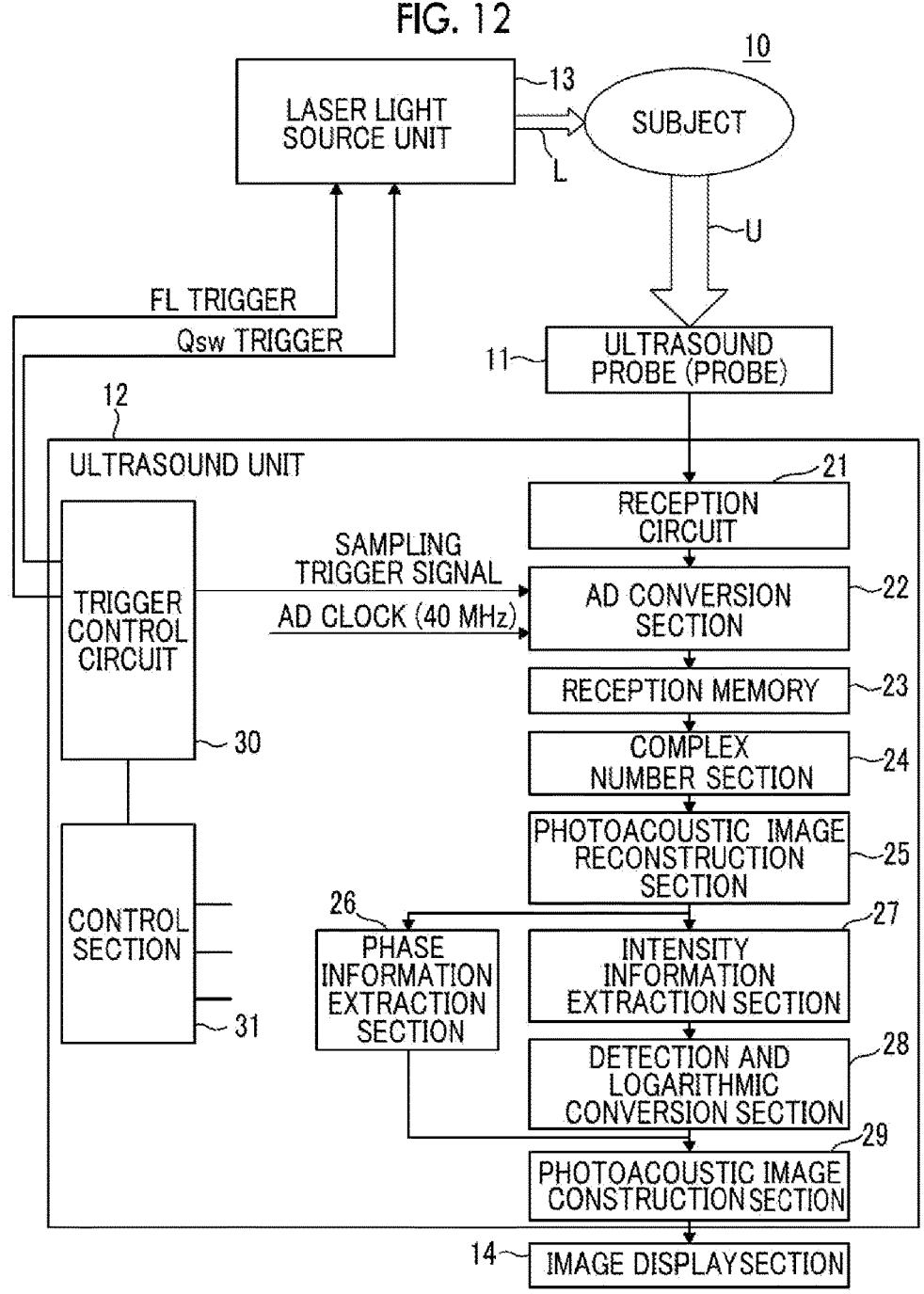
FIG. 12 is a schematic view showing the configuration of a photoacoustic measurement device according to an embodiment.

Next, an embodiment of a photoacoustic measurement device will be described. FIG. 12 is a schematic view showing the configuration of a photoacoustic measurement device 10 according to the embodiment. A photoacoustic measurement device 10 comprises an ultrasound probe (probe) 11, an ultrasound unit 12, and a laser light source unit 13 including a laser device of the invention. The laser light source unit 13 emits pulse laser light with which a subject is irradiated. The laser light source unit 13 emits laser light having a plurality of wavelengths including the first wavelength and the second wavelength.

For example, the laser light source unit 13 has the laser device 1 according to the first embodiment and light guide means (for example, an optical fiber or the like) which guides laser light emitted from the laser device 1. Laser light emitted from the laser light source unit 13 is guided to the probe 11 using the light guide means, and is irradiated from the probe 11 toward the subject. The irradiation position of laser light is not particularly limited, and irradiation of laser light may be performed from a location other than the probe 11. Inside the subject, an optical absorber absorbs energy of irradiated laser light, whereby an ultrasonic wave (photoacoustic wave) is generated. The probe 11 includes an ultrasound detector. The probe 11 has a plurality of ultrasound detector elements (ultrasound transducers) arranged in a one-dimensional manner, and detects an acoustic wave (photoacoustic signal) from the inside of the subject with the ultrasound transducers arranged in a one-dimensional manner.

The ultrasound unit 12 has a reception circuit 21, an AD conversion section 22, a reception memory 23, a complex number section 24, a photoacoustic image reconstruction section 25, a phase information extraction section 26, an intensity information extraction section 27, a detection and logarithmic conversion section 28, a photoacoustic image construction section 29, a trigger control circuit 30, and a control section 31. The reception circuit 21 receives the photoacoustic signal detected by the probe 11. The AD conversion section 22 is a detection section, samples the photoacoustic signal received by the reception circuit 21, and generates photoacoustic data as digital data. The AD conversion section 22 samples the photoacoustic signal in a predetermined sampling period in synchronization with an AD clock signal.

The AD conversion section 22 stores photoacoustic data in the reception memory 23. The AD conversion section 22 stores photoacoustic data corresponding to each wavelength of pulse laser light emitted from the laser light source unit 13 in the reception memory 23. That is, the AD conversion section 22 stores, in the reception memory 23, first photoacoustic data obtained by sampling a photoacoustic signal detected by the probe 11 when the subject is irradiated with pulse laser light having the first wavelength and second photoacoustic data obtained by sampling a photoacoustic signal detected by the probe 11 when the subject is irradiated with pulse laser light having the second wavelength.

The complex number section 24 reads first photoacoustic data and second photoacoustic data from the reception memory 23 and generates complex data in which one of first photoacoustic data and second photoacoustic data is a real part and the other photoacoustic data is an imaginary part. Hereinafter, description will be provided assuming that the complex number section 24 generates complex data in which first photoacoustic data is an imaginary part and second photoacoustic data is a real part.

The photoacoustic image reconstruction section 25 receives complex data from the complex number section 24 as input. The photoacoustic image reconstruction section 25 performs image reconstruction from input complex data using a Fourier transformation method (FTA method). In the image reconstruction using the Fourier transformation method, for example, a known method in the related art described in the document "Photoacoustic Image Reconstruction-A Quantitative Analysis" Jonathan I. Sperl et al. SPIE-OSA Vol. 6631 663103, or the like can be applied. The photoacoustic image reconstruction section 25 inputs data subjected to Fourier transformation indicating a reconstructed image to the phase information extraction section 26 and the intensity information extraction section 27.

The phase information extraction section 26 extracts the magnitude relationship of relative signal intensity between photoacoustic data corresponding to the respective wavelengths. In this embodiment, the phase information extraction section 26 has the reconstructed image reconstructed by the photoacoustic image reconstruction section 25 as input data and generates, from input data as complex data, phase information indicating which of the real part and the imaginary part is relatively large and how large the part is when comparing the real part and the imaginary part. For example, the phase information extraction section 26 generates $\theta=\tan^{-1}(Y/X)$ as phase information when complex data is represented by $X+iY$. In a case of $X=0$, it is assumed that $\theta=90°$. When second photoacoustic data (X) constituting the real part and first photoacoustic data (Y) constituting the imaginary part are equal, the phase information becomes $\theta=45°$. The phase information becomes closer to $\theta=0°$ when second photoacoustic data is relatively larger, and becomes closer to $\theta=90°$ when first photoacoustic data is relatively larger.

The intensity information extraction section 27 generates intensity information indicating signal intensity based on photoacoustic data corresponding to each wavelength. In this embodiment, the intensity information extraction section 27 has the reconstructed image reconstructed by the photoacoustic image reconstruction section 25 as input data and generates intensity information from input data as complex data. For example, the intensity information extraction section 27 extracts $(X^2+Y^2)^{1/2}$ as intensity information when complex data is represented by $X+iY$. The detection and logarithmic conversion section 28 generates the envelope of data indicating the intensity information extracted by the intensity information extraction section 27, and then, performs logarithmic conversion on the envelope to expand the dynamic range.

The photoacoustic image construction section 29 receives the phase information from the phase information extraction section 26 as input, and receives the intensity information after the detection and logarithmic conversion processing from the detection and logarithmic conversion section 28 as input. The photoacoustic image construction section 29 generates a photoacoustic image as a distribution image of the optical absorber based on the input phase information and intensity information. For example, the photoacoustic image construction section 29 determines the luminance (gradation value) of each pixel in the distribution image of the optical absorber based on the input intensity information. For example, the photoacoustic image construction section 29 determines the color (display color) of each pixel in the distribution image of the optical absorber based on the phase information. For example, the photoacoustic image construction section 29 determines the color of each pixel based on the input phase information using a color map in which a phase range of 0° to 90° corresponds to a predetermined color.

Since a phase range of 0° to 45° is a range in which second photoacoustic data is greater than first photoacoustic data, it is considered that the generation source of the photoacoustic signal is a vein in which blood primarily containing deoxygenated hemoglobin having greater absorption for the wavelength of 755 nm than absorption for the wavelength of 798 nm flows. Since a phase range of 45° to 90° is a range in which first photoacoustic data greater than second photoacoustic data, it is considered that the generation source of the photoacoustic signal is an artery in which blood primarily containing oxygenated hemoglobin having smaller absorption for the wavelength of 755 nm than absorption for the wavelength of 798 nm flows.

Accordingly, as the color map, for example, a color map in which the phase 0° is blue, color gradually changes to be colorless (white) when the phase becomes close to 45°, the phase 90° is red, and color gradually changes to be white when the phase becomes close to 45° is used. In this case, on the photoacoustic image, a portion corresponding to an artery can be represented in red, and a portion corresponding to a vein can be represented in blue. The gradation value may be constant, and color coding of the portion corresponding to the artery and the portion corresponding to the vein may be merely performed according to the phase information without using the intensity information. An image display section 14 displays the photoacoustic image generated by the photoacoustic image construction section 29 on a display screen.

The control section 31 performs control of the respective sections of the ultrasound unit 12. The trigger control circuit 30 outputs the flash lamp trigger for controlling light emission of the flash lamp 52 (see FIG. 1) to the laser light source unit 13. If the flash lamp trigger is received from the trigger control circuit 30, the control circuit 62 of the laser light source unit 13 transmits the flash lamp trigger to the flash lamp 52 to turn on the flash lamp 52, and makes excitation light be irradiated from the flash lamp 52 toward the laser rod 51. The control circuit 62 of the laser light source unit 13 outputs the Q switch trigger to the first Q-value change section 56 or the second Q-value change section 57 when the delay time set for each wavelength has elapsed after the output of the flash lamp trigger. The control circuit 62 changes the Q value of the first resonator from the low Q state to the high Q state when the oscillation wavelength is 800 nm. The control circuit 62 changes the Q values of the first resonator and the second resonator from the low Q state to the high Q state when the oscillation wavelength is 755 nm.

The trigger control circuit 30 outputs a sampling trigger (AD trigger) to the AD conversion section 22 in conformity with the timing of the Q switch trigger, that is, the emission timing of pulse laser light. The AD conversion section 22 starts sampling of the photoacoustic signal based on the sampling trigger.

Figure 13:
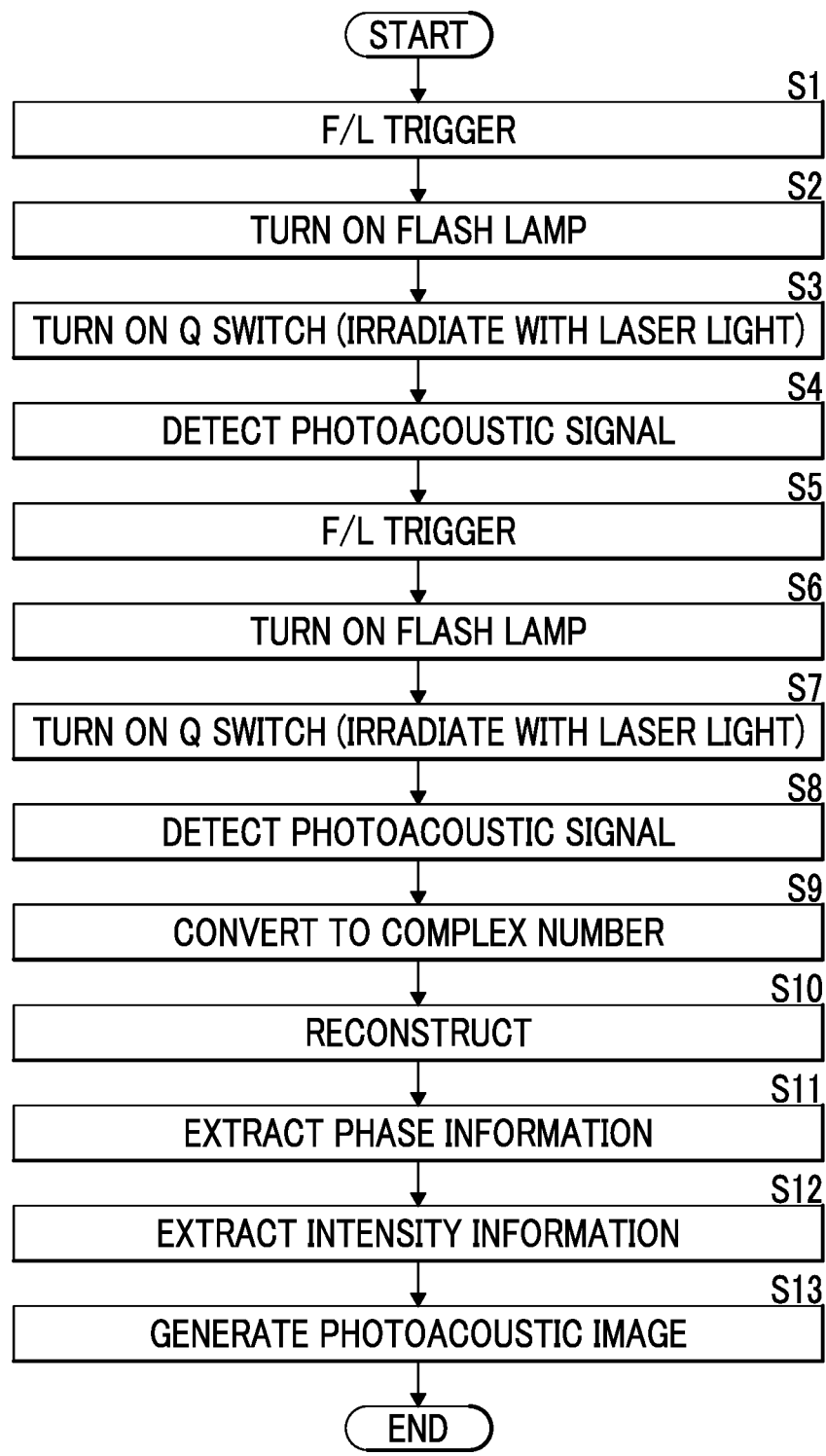
FIG. 13 is a flowchart showing an operation procedure of the photoacoustic measurement device.

Next, an operation procedure will be described. FIG. 13 shows an operation procedure of the photoacoustic measurement device 10. If the reception of the photoacoustic signal is prepared, the trigger control circuit 30 outputs the flash lamp trigger to the laser light source unit 13 in order to emit pulse laser light having the first wavelength (800 nm) (Step S1). The control circuit 62 of the laser light source unit 13 applies the first voltage to the first Q switch 58 before receiving the flash lamp trigger, and brings the first resonator C1 and the second resonator C2 into the low Q state. The control circuit 62 turns on the flash lamp 52 in response to the flash lamp trigger from the trigger control circuit 30 and excites the laser rod 51 (Step S2).

The control circuit 62 outputs the Q switch trigger to the first Q-value change section 56 or the second Q-value change section 57 when the delay time set for each wavelength has elapsed after the output of the flash lamp trigger and changes the applied voltage of the first Q switch 58 from the first voltage to 0 V (Step S3). At this time, the control circuit 62 applies 0 V to the second Q switch 60, the first resonator C1 is controlled in the high Q state, and the second resonator C2 is controlled in the low Q state. Of the first resonator and the second resonator, only the first resonator is brought into the high Q state, whereby the laser light source unit 13 emits pulse laser light having the wavelength of 800 nm. The control circuit 62 also transmits the Q switch trigger to the trigger control circuit 30, and informs the timing of the Q switch.

Pulse laser light having the wavelength of 800 nm emitted from the laser light source unit 13 is guided to, for example, the probe 11, and is irradiated from the probe 11 toward the subject. Inside the subject, the optical absorber absorbs energy of irradiated pulse laser light, whereby a photoacoustic signal is generated. The probe 11 detects the photoacoustic signal generated in the subject. The photoacoustic signal detected by the probe 11 is received by the reception circuit 21.

The trigger control circuit 30 outputs the sampling trigger to the AD conversion section 22 in conformity with the timing of the Q switch. The AD conversion section 22 samples the photoacoustic signal received by the reception circuit 21 in a predetermined sampling period (Step S4). The photoacoustic signal sampled by the AD conversion section 22 is stored in the reception memory 23 as first photoacoustic data.

If the reception of the next photoacoustic signal is prepared, the trigger control circuit 30 outputs the flash lamp trigger to the laser light source unit 13 in order to emit pulse laser light having the second wavelength (755 nm) (Step S5). The control circuit 62 applies the first voltage to the first Q switch 58 before receiving the flash lamp trigger, and brings the first resonator and the second resonator into the low Q state. The control circuit 62 turns on the flash lamp 52 in response to the flash lamp trigger from the trigger control circuit 30 and excites the laser rod 51 (Step S6).

The control circuit 62 outputs the Q switch trigger to the first Q-value change section 56 or the second Q-value change section 57 when the delay time set for each wavelength has elapsed after the output of the flash lamp trigger. The control circuit 62 changes the applied voltage of the first Q switch 58 from the first voltage to 0 V, and changes the applied voltage of the second Q switch 60 from 0 V to the fourth voltage (Step S7). At this time, the control circuit 62 changes the applied voltages of the first Q switch 58 and the second Q switch 60 simultaneously or first changes the applied voltage of the second Q switch 60, and then, changes the applied voltage of the first Q switch 58. The applied voltages of the first Q switch 58 and the second Q switch 60 are changed, whereby both of the first resonator C1 and the second resonator C2 are brought into the high Q state. When both resonators are in the high Q state, oscillation occurs at the wavelength of 755 nm with a high laser gain, and the laser light source unit 13 emits pulse laser light having the wavelength of 755 nm.

Pulse laser light having the wavelength of 755 nm emitted from the laser light source unit 13 is guided to, for example, the probe 11, and is irradiated from the probe 11 toward the subject. Inside the subject, the optical absorber absorbs energy of irradiated pulse laser light, whereby a photoacoustic signal is generated. The probe 11 detects the photoacoustic signal generated inside the subject. The photoacoustic signal detected by the probe 11 is received by the reception circuit 21.

The trigger control circuit 30 outputs the sampling trigger to the AD conversion section 22 in conformity with the timing of the Q switch. The AD conversion section 22 samples the photoacoustic signal received by the reception circuit 21 in a predetermined sampling period (Step S8). The photoacoustic signal sampled by the AD conversion section 22 is stored in the reception memory 23 as second photoacoustic data.

First and second photoacoustic data are stored in the reception memory, whereby data necessary for generating a photoacoustic image for one frame is arranged. In a case where a range in which a photoacoustic image is generated is divided into a plurality of partial regions, the processing of Steps S1 to S8 may be executed for each partial region.

The complex number section 24 reads first photoacoustic data and second photoacoustic data from the reception memory 23, and generates complex data in which first photoacoustic image data is an imaginary part and second photoacoustic image data is a real part (Step S9). The photoacoustic image reconstruction section 25 performs image reconstruction from complex data converted to a complex number in Step S9 using a Fourier transformation method (FTA method) (Step S10).

The phase information extraction section 26 extracts the phase information from the reconstructed complex data (reconstructed image) (Step S11). The phase information extraction section 26 extracts $\theta = \tan^{-1}(Y/X)$ as phase information, for example, when the reconstructed complex data is represented by $X+iY$ (however, in a case where $X=0$, $\theta=90°$). The intensity information extraction section 27 extracts the intensity information from the reconstructed complex data (Step S12). The intensity information extraction section 27 extracts $(X^2+Y^2)^{1/2}$ intensity information, for example, when the reconstructed complex data is represented by $X+iY$.

The detection and logarithmic conversion section 28 performs the detection and logarithmic conversion processing on the intensity information extracted in Step S12. The photoacoustic image construction section 29 generates the photoacoustic image based on the phase information extracted in Step S11 and information obtained by performing the detection and logarithmic conversion processing on the intensity information extracted in Step S12 (Step S13). The photoacoustic image construction section 29 determines the luminance (gradation value) of each pixel in the distribution image of the optical absorber based on, for example, the intensity information, and determines the color of each pixel based on the phase information, whereby the photoacoustic image is generated. The generated photoacoustic image is displayed on the image display section 14.

In the above description, although the subject is alternately irradiated with light having the wavelength of 800 nm and light having the wavelength of 755 nm, the invention is not limited thereto. A repetition frequency of oscillation at the wavelength of 800 nm may be set to be higher than a repetition frequency of oscillation at the wavelength of 755 nm. For example, light having the wavelength of 800 nm may be continuously emitted multiple times after light having the wavelength of 755 nm has been emitted from the laser light source unit 13. In this case, a photoacoustic signal for light having the wavelength of 800 nm may be acquired multiple times, and processing, such as addition and averaging, may be performed on multiple photoacoustic signals. In this way, it is possible to increase a signal-to-noise ratio of the photoacoustic image at the wavelength of 800 nm. As a result, it is possible to improve image quality of separation and extraction of a vein/artery obtained using the difference in contrast from a photoacoustic signal for light having the wavelength of 755 nm, or to improve calculation accuracy of oxygen saturation.

As described above, since the photoacoustic measurement device 10 of this embodiment uses the laser device 1 according to the first embodiment, the same effects as those in the first embodiment are obtained.

In this embodiment, complex data in which one of first photoacoustic data and second photoacoustic data obtained at two wavelengths is a real part and the other photoacoustic data is an imaginary part is generated, and the reconstructed image is generated from complex data by the Fourier transformation method. In such a case, it is possible to efficiently perform reconstruction compared to a case where first photoacoustic data and second photoacoustic data are individually reconstructed. Pulse laser light having a plurality of wavelengths is irradiated, and a photoacoustic signal (photoacoustic data) when pulse laser light having each wavelength is irradiated is used, whereby it is possible to perform functional imaging using the fact that the optical absorption characteristic of each optical absorber is different according to the wavelength.

In the photoacoustic measurement device 10 of this embodiment, an ultrasonic wave may be transmitted from the probe 11 to the subject, and a reflected acoustic wave image may be generated based on a signal of a reflected wave of the transmitted acoustic wave (ultrasonic wave). The reflected acoustic wave image (ultrasound image) is generated in addition to the photoacoustic image, and the ultrasound image is referred to, whereby it is possible to observe a portion which cannot be imaged in the photoacoustic image.

EXPLANATION OF REFERENCES

1, 2, 3: laser device
10: photoacoustic measurement device
11: probe
12: ultrasound unit
13: laser light source unit
14: image display section
21: reception circuit
22: AD conversion section
23: reception memory
24: complex number section
25: photoacoustic image reconstruction section
26: phase information extraction section
27: intensity information extraction section
28: detection and logarithmic conversion section
29: photoacoustic image construction section
30: trigger control circuit
31: control section
51: laser rod
52: flash lamp
53, 54, 55: mirror
56, 57: Q-value change section
62: control circuit
C1: resonator
C2: resonator
L: laser light

What is claimed is:

1. A laser device comprising:
   a solid-state laser medium which has oscillation wavelengths at a first wavelength and a second wavelength with higher light emission efficiency than at the first wavelength;
   an excitation section which excites the laser medium;
   a first resonator which is a resonator oscillating light having the first wavelength and has the laser medium on an internal optical path;

a second resonator which is a resonator oscillating light having the second wavelength and has a common optical path which is an optical path in common for the first resonator including an optical path, on which the laser medium is disposed;

a Q-value change unit which includes at least a Q-value change part disposed on the common optical path and oscillates light having the first wavelength or light having the second wavelength through Q switching; and a control section which controls the excitation section and the Q-value change unit, wherein the control section controls the Q-value change unit to oscillate light having the first wavelength through Q switching when a first delay time has elapsed after the excitation of the laser medium has been started in a case where the oscillation wavelength is the first wavelength, the control section controls the Q-value change unit to oscillate light having the second wavelength through Q switching when a second delay time, at which the intensity of light having the second wavelength is less than maximum intensity, has elapsed after the excitation of the laser medium has been started in a case where the oscillation wavelength is the second wavelength, and the control section changes the set value of the first delay time or the second delay time according to the amount of excitation energy applied to the laser medium by the excitation section.

2. The laser device according to claim 1, wherein the first delay time and the second delay time are set to values such that the intensity of light having the first wavelength and the intensity of light having the second wavelength are equal to each other.

3. The laser device according to claim 1, wherein the first delay time is set to a value such that the intensity of light having the first wavelength becomes the maximum intensity.

4. The laser device according to claim 1, wherein the excitation section includes a flash lamp as an excitation light source, and the control section changes the set value of the first delay time or the second delay time according to a charging voltage of the flash lamp.

5. The laser device according to claim 4, wherein the control section has a first reference table in which the charging voltage and the set value of the first delay time or the second delay time are associated with each other, and changes the set value of the first delay time or the second delay time based on the first reference table.

6. The laser device according to claim 1, wherein the excitation section includes an excitation light source, and the control section changes the set value of the first delay time or the second delay time according to a use duration of the excitation light source.

7. The laser device according to claim 6, wherein the control section has a second reference table in which the use duration and the set value of the first delay time or the second delay time are associated with each other, and changes the set value of the first delay time or the second delay time based on the second reference table.

8. A laser device comprising:

a solid-state laser medium which has oscillation wavelengths at a first wavelength and a second wavelength with higher light emission efficiency than at the first wavelength;

an excitation section which excites the laser medium;

a first resonator which is a resonator oscillating light having the first wavelength and has the laser medium on an internal optical path;

a second resonator which is a resonator oscillating light having the second wavelength and has a common optical path which is an optical path in common for the first resonator including an optical path, on which the laser medium is disposed;

a Q-value change unit which includes at least a Q-value change part disposed on the common optical path and oscillates light having the first wavelength or light having the second wavelength through Q switching; and a control section which controls the excitation section and the Q-value change unit, wherein the control section controls the Q-value change unit to oscillate light having the first wavelength through Q switching when a first delay time has elapsed after the excitation of the laser medium has been started in a case where the oscillation wavelength is the first wavelength, the control section controls the Q-value change unit to oscillate light having the second wavelength through Q switching when a second delay time, at which the intensity of light having the second wavelength is less than maximum intensity, has elapsed after the excitation of the laser medium has been started in a case where the oscillation wavelength is the second wavelength, the first resonator is constituted of a first mirror and a second mirror opposed to each other with the laser medium sandwiched therebetween, the second resonator is constituted of the first mirror and a third mirror opposed to the first mirror with the laser medium and the second mirror sandwiched therebetween, the Q-value change unit is constituted of a first Q-value change section which is disposed on the common optical path, and a second Q-value change section which is disposed between the second mirror and the third mirror, and at least one of the first mirror, the second mirror, and the third mirror is movable along an optical axis direction.

9. The laser device according to claim 8, wherein the control section changes the set value of the first delay time according to the resonator length of the first resonator or changes the set value of the second delay time according to the resonator length of the second resonator.

10. The laser device according to claim 9, wherein the control section has a third reference table in which the resonator length of the first resonator and the set value of the first delay time are associated with each other and a fourth reference table in which the resonator length of the second resonator and the set value of the second delay time are associated with each other, changes the set value of the first delay time based on the third reference table, and changes the set value of the second delay time based on the fourth reference table.

11. A laser device comprising:

a solid-state laser medium which has oscillation wavelengths at a first wavelength and a second wavelength with higher light emission efficiency than at the first wavelength;

an excitation section which excites the laser medium;

a first resonator which is a resonator oscillating light having the first wavelength and has the laser medium on an internal optical path;

a second resonator which is a resonator oscillating light having the second wavelength and has a common optical path which is an optical path in common for the first resonator including an optical path, on which the laser medium is disposed;

a Q-value change unit which includes at least a Q-value change part disposed on the common optical path and oscillates light having the first wavelength or light having the second wavelength through Q switching; and a control section which controls the excitation section and the Q-value change unit, wherein the control section controls the Q-value change unit to oscillate light having the first wavelength through Q switching when a first delay time has elapsed after the excitation of the laser medium has been started in a case where the oscillation wavelength is the first wavelength, the control section controls the Q-value change unit to oscillate light having the second wavelength through Q switching when a second delay time, at which the intensity of light having the second wavelength is less than maximum intensity, has elapsed after the excitation of the laser medium has been started in a case where the oscillation wavelength is the second wavelength, the first resonator is constituted of a first mirror and a second mirror opposed to each other with the laser medium sandwiched therebetween, the second resonator is constituted of the first mirror and a third mirror opposed to the first mirror with the laser medium and the second mirror sandwiched therebetween, the Q-value change unit is constituted of a first Q-value change section which is disposed on the common optical path, and a second Q-value change section which is disposed between the second mirror and the third mirror, and the control section switches the drive states of the first Q-value change section and the second Q-value change section among a first drive state where the Q values of the first resonator and the second resonator are in a low Q state lower than an oscillation threshold, a second drive state where the Q values of the first resonator and the second resonator are in a high Q state higher than the oscillation threshold, and a third drive state where the Q value of the first resonator is in the high Q state and the Q value of the second resonator is in the low Q state.

12. The laser device according to claim 11, wherein the control section brings the drive states of the first Q-value change section and the second Q-value change section into the first drive state at the time of the excitation of the laser medium.

13. The laser device according to claim 12, wherein the control section switches the drive states of the first Q-value change section and the second Q-value change section from the first drive state to the third drive state in a case where the oscillation wavelength is the first wavelength after the excitation of the laser medium, and the control unit switches the drive states of the first Q-value change section and the second Q-value change section from the first drive state to the second drive state in a case where the oscillation wavelength is the second wavelength.

14. The laser device according to claim 8, wherein the first Q-value change section includes a first Q switch which changes the Q value of the first resonator according to an applied voltage, the second Q-value change section includes a second Q switch which changes the Q value of the second resonator according to an applied voltage, and the control section drives the first Q-value change section or the second Q-value change section by controlling the applied voltage.

15. A photoacoustic measurement device comprising:

the laser device according to claim 1; and a probe which detects a photoacoustic wave generated in a subject using laser light emitted from the laser device.

16. The photoacoustic measurement device according to claim 15, further comprising:

a signal processing section which processes a signal of the photoacoustic wave detected using the probe.

17. The photoacoustic measurement device according to claim 16, wherein the signal processing section has an acoustic image generation section which generates a photoacoustic image based on the signal of the photoacoustic wave.

18. The photoacoustic measurement device according to claim 17, wherein the acoustic image generation section generates a reflected acoustic image based on a signal of a reflected wave of an acoustic wave transmitted to the subject.

* * * * *